United States Patent
Janssens et al.

(10) Patent No.: US 7,528,149 B2
(45) Date of Patent: May 5, 2009

(54) RESPIRATORY SYNCYTIAL VIRUS REPLICATION INHIBITORS

(75) Inventors: Frans Eduard Janssens, Bonneiden (BE); Kathleen Petrus Marie-José Meersman, Wechelderzande (BE); François Maria Sommen, Wortel (BE); Koenraads Jozef Lodewijk Marcell Andries, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/625,648

(22) Filed: Jan. 22, 2007

(65) Prior Publication Data

US 2007/0135404 A1  Jun. 14, 2007

Related U.S. Application Data

(62) Division of application No. 10/817,472, filed on Apr. 2, 2004, now Pat. No. 7,179,811, which is a division of application No. 10/019,380, filed as application No. PCT/EP00/05675 on Jun. 20, 2000, now Pat. No. 6,747,028.

(30) Foreign Application Priority Data

Jun. 1, 1999  (EP)  ................................... 99202088

(51) Int. Cl.
C07D 471/04  (2006.01)
A61K 31/437  (2006.01)

(52) U.S. Cl. .................. 514/303; 514/256; 514/252.04; 514/253.04; 544/238; 544/333; 544/362; 546/118

(58) Field of Classification Search ................ 544/238, 544/333, 362; 546/118; 514/303, 256, 252.04, 514/253.04
See application file for complete search history.

(56) References Cited

U.S. PATENT DOCUMENTS

| | | | |
|---|---|---|---|
| 4,634,704 A | 1/1987 | Janssens et al. | 514/253 |
| 4,695,569 A | 9/1987 | Janssens et al. | 514/258 |
| 5,360,807 A | 11/1994 | Janssens et al. | 514/318 |
| 6,747,028 B1 | 6/2004 | Janssens et al. | 514/252.02 |
| 7,179,811 B2 | 2/2007 | Janssens et al. | 514/252.04 |

FOREIGN PATENT DOCUMENTS

| | | |
|---|---|---|
| EP | 0747363 A1 | 12/1966 |
| EP | 0005318 A1 | 11/1979 |
| EP | 0099139 A2 | 1/1984 |
| EP | 0144101 A2 | 6/1985 |
| EP | 0145037 A2 | 6/1985 |
| EP | 0151824 A2 | 8/1985 |
| EP | 0151826 A1 | 8/1985 |
| EP | 0232937 A2 | 8/1987 |
| EP | 0295742 A1 | 12/1988 |
| EP | 0297661 A1 | 1/1989 |
| EP | 0307014 A1 | 3/1989 |
| EP | 0282133 B1 | 7/1993 |
| WO | 9201687 A1 | 2/1992 |
| WO | 9201697 A1 | 2/1992 |
| WO | 9810764 A1 | 3/1998 |
| WO | 9831363 A1 | 7/1998 |
| WO | 9855120 A1 | 12/1998 |

OTHER PUBLICATIONS

Akula, M. R. et al., "An Improved Synthesis of 3-Phenyl-and 3-Methoxyquinaldine," *Org. Prep. Proced. Int.*, 1991, 23, pp. 386-387.
Ceré, V. et al., "Catalytic Hydrogenation of Benzo[2.1.3]Oxadiazoles," *Tetrahedron*, 1972, 28, 3271-3276.
Chiba, T. et al., "Inhibitory Effect of Pyridobenzazoles on Virus Replication in vitro," *Biol Pharm Bull*, 1995, 18(8), 1081-1083.
Goodman and Gilman, "Biotransformation of Drugs," in *The Pharmacological Basis of Therapeutics*, 8th ed., McGraw-Hill, Int. Ed. 1992, 13-15.
Greene, T. et al., *Protective Groups in Organic Synthesis*, John Wiley & Sons Inc., 1991, Chapter 7.
Lindström, S. et al., "Synthesis of the Mutagenic 2-Amino-1,6-Dimethyl-Imidazo[4,5-b]Pyridine (1,6-DMIP) and Five of Its Isomers," *Heterocycles*, 1994, 38(3), 529-540.
Richardson, Jr. et al. "Study of the Synthesis and Chemistry of the 5,6-Dihydroimidazo[ij]quinoline Series," *J. Org. Chem.*, 1960, 25, 1138-1147.
Tidwell, R. et al., "Aromatic Amidines: Comparison of Their Ability to Block Respiratory Syncytial Virus Induced Cell Fusion and to Inhibit Plasmin, Urokinase, Thrombin, and Trypsin," *J Med Chem*, 1983, 26, 294-298.
Wyde et al., "CL387626 exhibits marked and unusual antiviral activity against respiratory syncytial virus in tissue culture and in cotton rats," *Antivirus Research*, 1998, 38, 31-42.

*Primary Examiner*—Kahsay T Habte
(74) *Attorney, Agent, or Firm*—Woodcock Washburn LLP

(57) ABSTRACT

This invention concerns compounds of formula (I)

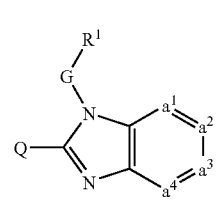

prodrugs, addition salts, or stereochemically isomeric forms thereof for use as, inter alia, respiratory syncytial virus replication inhibitors; their preparation, compositions containing them and methods of their use in treating respiratory syncytial viral infections.

15 Claims, No Drawings

RESPIRATORY SYNCYTIAL VIRUS REPLICATION INHIBITORS

CROSS-REFERENCE TO RELATED APPLICATIONS

This Application is a divisional application of U.S. application Ser. No. 10/817,472, filed Apr. 2, 2004 (now allowed), which is a divisional application of U.S. application Ser. No. 10/019,380, filed Dec. 27, 2001, now U.S. Pat. No. 6,747,028, which is the national stage entry under 35 U.S.C. § 371 of PCT/EP00/05675, filed Jun. 20, 2000 in English, which claims priority to EPO 99202088.3, filed Jun. 28, 1999, the disclosures of which are incorporated herein by reference in their entirety.

The present invention is concerned with benzimidazoles and imidazopyridines having antiviral activity, in particular, they have an inhibitory activity on the replication of the respiratory syncytial virus. It further concerns their preparation and compositions comprising them, as well as their use as a medicine.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. Ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

EP-A-0,005,138, EP-A-0,099,139, EP-A-0,145,037, EP-A-0,144,101, EP-A-0,151,826, EP-A-0,151,824, EP-A-0,232,937, EP-A-0,295,742, EP 0,297,661, EP-A-0,307,014, WO 92 01697 describe benzimidazole and imidazopyridine substituted piperidine and piperazine derivatives as antihistaminics, antiallergics or serotonine antagonists.

The present invention concerns the compounds of formula (I)

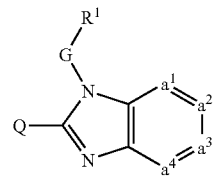

their prodrugs, N-oxides, addition salts, quaternary amines, metal complexes and stereochemically isomeric forms wherein $-a^1=a^2-a^3=a^4-$ represents a bivalent radical of formula

| | |
|---|---|
| —CH=CH—CH=CH— | (a-1); |
| —N=CH—CH=CH— | (a-2); |
| —CH=N—CH=CH— | (a-3); |
| —CH=CH—N=CH— | (a-4); or |
| —CH=CH—CH=N— | (a-5); | wherein each hydrogen atom in the radicals (a-1), (a-2), (a-3), (a-4) and (a-5) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, mono- or di($C_{1-4}$alkyl)amino$C_{1-6}$alkyl, $C_{1-6}$alkyloxycarbonyl, hydroxy$C_{1-6}$alkyl, or a radical of formula

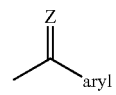

wherein =Z is =O, =CH—C(=O)—$NR^{5a}R^{5b}$, =$CH_2$, =CH—$C_{1-6}$alkyl, =N—OH or =N—O—$C_{1-6}$ alkyl;

Q is a radical of formula

 (b-1)

 (b-2)

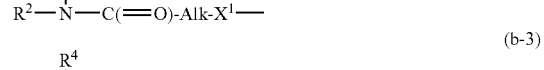 (b-3)

 (b-4)

 (b-5)

-continued

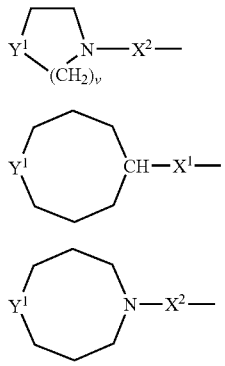

wherein Alk is $C_{1-6}$alkanediyl;
Y$^1$ is a bivalent radical of formula —NR$^2$— or —CH(NR$^2$R$^4$)—;
X$^1$ is NR$^4$, S, S(=O), S(=O)$_2$, O, CH$_2$, C(=O), C(=CH$_2$), CH(OH), CH(CH$_3$), CH(OCH$_3$), CH(SCH$_3$), CH(NR$^{5a}$R$^{5b}$), CH$_2$—NR$^4$ or NR$^4$—CH$_2$;
X$^2$ is a direct bond, CH$_2$, C(=O), NR$^4$, $C_{1-4}$alkyl-NR$^4$, NR$^4$—$C_{1-4}$alkyl;
t is 2, 3, 4 or 5;
u is 1, 2, 3, 4 or 5;
v is 2 or 3; and
whereby each hydrogen atom in Alk and the carbocycles and the heterocycles defined in radicals (b-3), (b-4), (b-5), (b-6), (b-7) and (b-8) may optionally be replaced by R$^3$; with the proviso that when R$^3$ is hydroxy or $C_{1-6}$alkyloxy, then R$^3$ can not replace a hydrogen atom in the α position relative to a nitrogen atom;
G is $C_{1-10}$alkanediyl substituted with one or more hydroxy, $C_{1-6}$alkyloxy, aryl$C_{1-6}$alkyloxy, $C_{1-6}$alkylthio, aryl$C_{1-6}$alkylthio, HO(—CH$_2$—CH$_2$—O)$_n$—, $C_{1-6}$alkyloxy(—CH$_2$—CH$_2$—O)$_n$— or aryl$C_{1-6}$alkyloxy(—CH$_2$—CH$_2$—O)$_n$—;
R$^1$ is a monocyclic heterocycle or aryl; said heterocycle being selected from piperidinyl, piperazinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl; and each heterocycle may optionally be substituted with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-SO$_2$—NR$^{5c}$—, aryl-SO$_2$—NR$^{5c}$—, $C_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, aryl$C_{1-6}$alkyloxy(—CH$_2$—CH$_2$—O)$_n$— and mono- or di($C_{1-6}$alkyl)amino(—CH$_2$—CH$_2$—O)$_n$—;
each n independently is 1, 2, 3 or 4;
R$^2$ is hydrogen, formyl, $C_{1-6}$alkylcarbonyl, Hetcarbonyl, pyrrolidinyl, piperidinyl, homopiperidinyl, $C_{3-7}$cycloalkyl substituted with N(R$^6$)$_2$, or $C_{1-10}$alkyl substituted with N(R$^6$)$_2$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;

R$^3$ is hydrogen, hydroxy, $C_{1-6}$alkyl, $C_{1-6}$alkyloxy, aryl$C_{1-6}$alkyl or aryl$C_{1-6}$alkyloxy;
R$^4$ is hydrogen, $C_{1-6}$alkyl or aryl$C_{1-6}$alkyl;
R$^{5a}$, R$^{5b}$, R$^{5c}$ and R$^{5d}$ each independently are hydrogen or $C_{1-6}$alkyl; or
R$^{5a}$ and R$^{5b}$, or R$^{5c}$ and R$^{5d}$ taken together form a bivalent radical of formula —(CH$_2$)$_s$— wherein s is 4 or 5;
R$^6$ is hydrogen, $C_{1-4}$alkyl, formyl, hydroxy$C_{1-6}$alkyl, $C_{1-6}$alkylcarbonyl or $C_{1-6}$alkyloxycarbonyl;
aryl is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;
Het is pyridyl, pyrimidinyl, pyrazinyl, pyridazinyl.

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated.

As used herein $C_{1-3}$alkyl as a group or part of a group defines straight or branched chain saturated hydrocarbon radicals having from 1 to 3 carbon atoms such as methyl, ethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl and the like; $C_{2-4}$alkyl as a group or part of a group defines straight or branched chain saturated hydrocarbon radicals having from 2 to 4 carbon atoms such as ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, octyl, nonyl, 2-methylhexyl, 2-methylheptyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl and the like. $C_{3-7}$cycloalkyl is generic to cyclopropyl, cyclobutyl, cyclopentyl, cyclohexyl and cycloheptyl; $C_{2-5}$alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, $C_{2-5}$alkanediyl is substituted on $C_{1-10}$alkyl as provided for in the definition of R$^2$, it is meant to be substituted on one carbon atom thus forming a spiro moiety; $C_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; $C_{1-6}$alkanediyl is meant to include $C_{1-4}$alkanediyl and the higher homologues thereof having from 5 to 6 carbon atoms such as, for example, 1,5-pentanediyl, 1,6-hexanediyl and the like; $C_{1-10}$alkanediyl is meant to include $C_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom. The term (=N—OH) forms a hydroxylimine moiety when attached to a carbon atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-4}$alkyl, they may be the same or different.

When any variable (e.g. aryl, $R^2$, $R^3$, $R^4$, $R^{5a}$, $R^{5b}$ etc.) occurs more than one time in any constituent, each definition is independent.

It will be appreciated that some of the compounds of formula (I) and their prodrugs, N-oxides, addition salts, quaternary amines, metal complexes and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their prodrugs, N-oxides, addition salts, quaternary amines, metal complexes or physiologically functional derivatives may possess. Unless otherwise mentioned or indicated, the chemical designation of compounds denotes the mixture of all possible stereo-chemically isomeric forms, said mixtures containing all diastereomers and enantiomers of the basic molecular structure as well as each of the individual isomeric forms of formula (I) and their prodrugs, N-oxides, salts, solvates or quaternary amines substantially free, i.e. associated with less than 10%, preferably less than 5%, in particular less than 2% and most preferably less than 1% of the other isomers. Stereochemically isomeric forms of the compounds of formula (I) are obviously intended to be embraced within the scope of this invention. As used hereinafter the terms R or S are well-known by the person skilled in the art For some of the compounds of formula (I), their prodrugs, N-oxides, salts, solvates, quaternary amines, or metal complexes and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

A special group of corn pounds are those compounds of formula (I) wherein one or more of the following restrictions apply:

Q is a radical of formula (b-1), (b-3), (b-4), (b-5), (b-6), (b-7) or (b-8);

$X^2$ is a direct bond, $CH_2$ or $C(=O)$;

$R^2$ is hydrogen, pyrrolidinyl, piperidinyl, homopiperidinyl, $C_{3-7}$cycloalkyl substituted with $NHR^6$, or $C_{1-10}$alkyl substituted with $NHR^6$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy or aryl$C_{1-6}$alkyl;

$R^6$ is hydrogen, $C_{1-4}$alkyl, formyl, $C_{1-6}$alkylcarbonyl or $C_{1-6}$alkyloxycarbonyl.

Also an interesting group of compounds are those compounds of formula (I) wherein one or more of the following restrictions apply:
-$a^1$=$a^2$-$a^3$=$a^4$- is a radical of formula (a-1) or (a-2);
$R^1$ is phenyl optionally substituted with halo, $C_{1-6}$alkyl or $C_{1-4}$alkyloxy; or pyridyl optionally substituted with 1 or more substituents selected from aryl$C_{1-6}$alkyloxy, $C_{1-6}$alkyloxy$C_{1-6}$alkyl, aryl, mono- or di($C_{1-6}$alkyl)amino, C(=O)—$NR^{5c}R^{5d}$, halo or $C_{1-6}$alkyl;
G is $C_{1-4}$alkanediyl substituted with hydroxy, $C_{1-6}$alkyloxy, HO(—$CH_2$—$CH_2$—O)$_n$—, $C_{1-6}$alkyloxy(—$CH_2$—$CH_2$—O)$_n$— or aryl$C_{1-6}$alkyloxy(—$CH_2$—$CH_2$—O)$_n$—;
Q is a radical of formula (b-5) wherein v is 2, and $Y^1$ is N—$R^2$;
$X^1$ is NH or $CH_2$;
$R^2$ is hydrogen or $C_{1-10}$alkyl susbstituted with $NHR^6$ wherein $R^6$ is hydrogen or $C_{1-6}$alkyloxycarbonyl.

Particular compounds are those compounds of formula (I) wherein $R^2$ is $C_{1-10}$alkyl substituted with $NH_2$.

Other particular compounds are those compounds of formula (I) wherein G is methylene or 1,2-ethanediyl, both substituted with hydroxy, $C_{1-6}$alkyloxy, HO(—$CH_2$—$CH_2$—O)$_n$—, $C_{1-6}$alkyloxy(—$CH_2$—$CH_2$—O)$_n$— or aryl$C_{1-6}$alkyloxy(—$CH_2$—$CH_2$—O)$_n$—.

Also particular compounds are those compounds of formula (I) wherein $R^1$ is pyridyl, preferably 2-pyridyl, substituted with one or 2 substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{5c}$—, aryl-$SO_2$—$NR^{5c}$—, $C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$— and mono- or di($C_{1-6}$alkyl)amino(—$CH_2$—$CH_2$—O)$_n$—, preferably selected from aryl$C_{1-6}$alkyloxy, $C_{1-6}$alkyloxy$C_{1-6}$alkyl, aryl, mono- or di($C_{1-6}$alkyl)amino, C(=O)—$NR^{5a}R^{5b}$, halo or $C_{1-6}$alkyl.

Preferred compounds are those compounds of formula (I) wherein $R^1$ is an optionally substituted 2-pyridyl moiety, in particular, a 2-pyridyl, a 6-substituted-2-pyridyl or a 3,6-disubstituted-2-pyridyl moiety.

Preferred compounds are
[(A),(S)]-N-[1-(2-amino-3-methylbutyl)-4-piperidinyl]-1-[(6-bromo-2-pyridinyl)-ethoxymethyl]-1H-benzimidazol-2-amine (compound 69);
[(A),(S)]-N-[1-(2-aminopropyl)-4-piperidinyl]-1-[ethoxy(6-methyl-2-pyridinyl)methyl]-1H-benzimidazol-2-amine (compound 75);
(±)-N-[1-(2-amino-3-methylbutyl)-4-piperidinyl]-1-[(2-methoxyethoxy)(6-methyl-2-pyridinyl)methyl]-1H-benzimidazol-2-amine (compound 86);
N-[1-(2-amino-3-methylbutyl)-4-piperidinyl]-6-chloro-1-[(2-methoxyethoxy)(6-methyl-2-pyridinyl)methyl]-4-methyl-1H-benzimidazol-2-amine trihydrochloride trihydrate (compound 88);
[(A),(R)]-N-[1-(2-amino-3-methylbutyl)-4-piperidinyl]-1-[ethoxy(6-methyl-2-pyridinyl)methyl]-1H-benzimidazol-2-amine monohydrate (compound 68);
(±)-N-[1-(2-aminopropyl)-4-piperidinyl]-1-[ethoxy(6-methyl-2-pyridinyl)methyl]-1H-benzimidazol-2-amine (compound 12);
[(A)(S)]-N-[1-(2-amino-3-methylbutyl)-4-piperidinyl]-1-[ethoxy(6-methyl-2-pyridinyl)methyl]-1H-benzimidazol-2-amine monohydrate (compound 67);
(±)-N-[1-(2-amino-3-methylbutyl)-4-piperidinyl]-1-[ethoxy(6-methyl-2-pyridinyl)methyl]-1-H-benzimidazol-2-amine (compound 83);
[(A),(R)]-N-[1-(2-aminopropyl)-4-piperidinyl]-1-[ethoxy(6-methyl-2-pyridinyl)methyl]-1H-benzimidazol-2-amine monohydrate (compound 74);
(±)-N-[1-(2-aminoethyl)-4-piperidinyl]-1-[(6-bromo-2-pyridinyl)ethoxymethyl]-2-benzimidazol-2-amine (compound 9);
(±)-N-[1-(2-aminoethyl)-4-piperidinyl]-1-[(2-ethoxyethoxy)(6-methyl-2-pyridinyl)methyl]-1H-benzimidazol-2-amine (compound 64);
[(B),(S)]N-[1-(2-aminopropyl)-4-piperidinyl]-1-[ethoxy(6-methyl-2-pyridinyl)methyl]-1H-benzimidazol-2-amine monohydrate (compound 76);
(±)-N-[1-(2-amino-3-methylbutyl)-4-piperidinyl]-3-[(2-methoxyethoxy)(6-methyl-2-pyridinyl)methyl]-7-methyl-3H-imidazo[4,5-b]pyridin-2-amine (compound 89);
(±)-N-[1-(2-amino-3-methylbutyl)-4-piperidinyl]-1-[(2-ethoxyethoxy)(6-phenyl-2-pyridinyl)methyl]-1H-benzimidazol-2-amine (compound 85);
(±)-N-[1-(2-aminoethyl)-4-piperidinyl]-1-[(2-methoxyethoxy)(6-methyl-2-pyridinyl)-methyl]-1H-benzimidazol-2-amine (compound 82);
the prodrugs, N-oxides, addition salts, quaternary amines, metal complexes and stereochemically isomeric forms thereof.

Most preferred are
(±)-N-[1-(2-amino-3-methylbutyl)-4-piperidinyl]-1-[(6-bromo-2-pyridinyl)ethoxymethyl]-4-methyl-1H-benzimidazol-2-amine monohydrate (compound 87);
[(A),(R)]-N-[1-(2-amino-3-methylbutyl)-4-piperidinyl]-1-[(6-bromo-2-pyridinyl)ethoxymethyl]-1H-benzimidazol-2-amine (compound 70);
(±)-N-[1-(2-amino-3-methylbutyl)-4-piperidinyl]-1-[(6-bromo-2-pyridinyl)ethoxymethyl]-1H-benzimidazol-2-amine (compound 10);
the prodrugs, N-oxides, addition salts, quaternary amines, metal complexes and stereochemically isomeric forms thereof.

In general, compounds of formula (I) can be prepared by reacting an intermediate of formula (II-a) or (II-b), wherein P represents a protecting group, such as, for example $C_{1-4}$alkyloxycarbonyl, or those protecting groups mentioned in Chapter 7 of 'Protective Groups in Organic Synthesis' by T Greene and P. Wuyts (John Wiley & Sons Inc., 1991), with an intermediate of formula (III), wherein $W_1$ is a suitable leaving group, such as a halo atom, e.g. chloro, bromo, in the presence of a suitable base, such as, e.g. sodium hydride. Said reaction can be performed in a reaction-inert solvent, such as N,N-dimethylformamide.

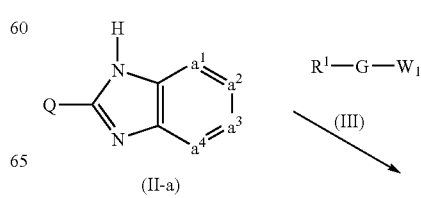

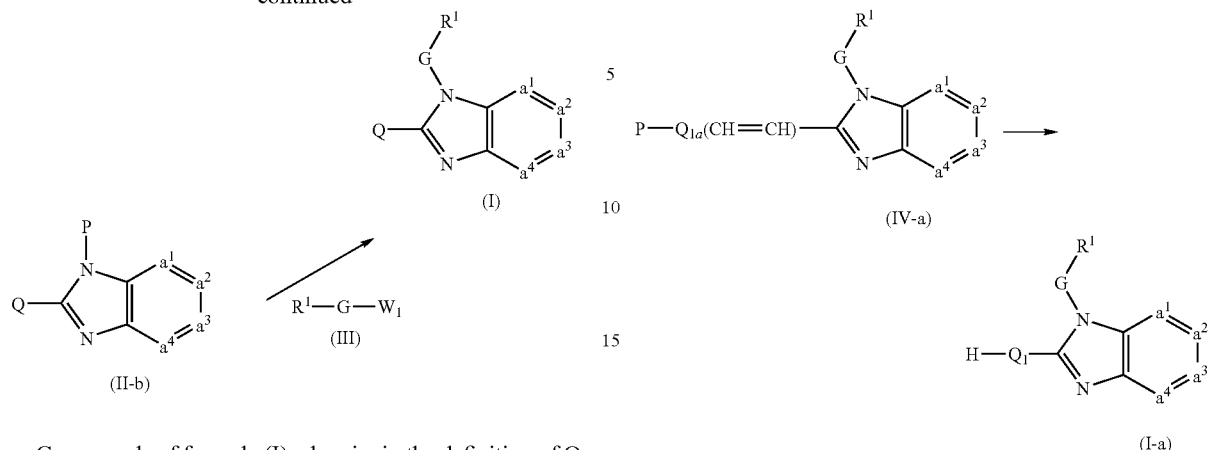

Compounds of formula (I) wherein, in the definition of Q, $R^2$ or at least one $R^6$ substituent is hydrogen, said Q being represented by H-$Q_1$, and said compounds being represented by formula (I-a), can be prepared by deprotecting an intermediate of formula (IV) wherein P represents a protecting group, for example $C_{1-4}$alkyloxycarbonyl, benzyl, or those protecting groups mentioned in Chapter 7 of 'Protective Groups in Organic Synthesis' by T Greene and P. Wuyts (John Wiley & Sons Inc., 1991).

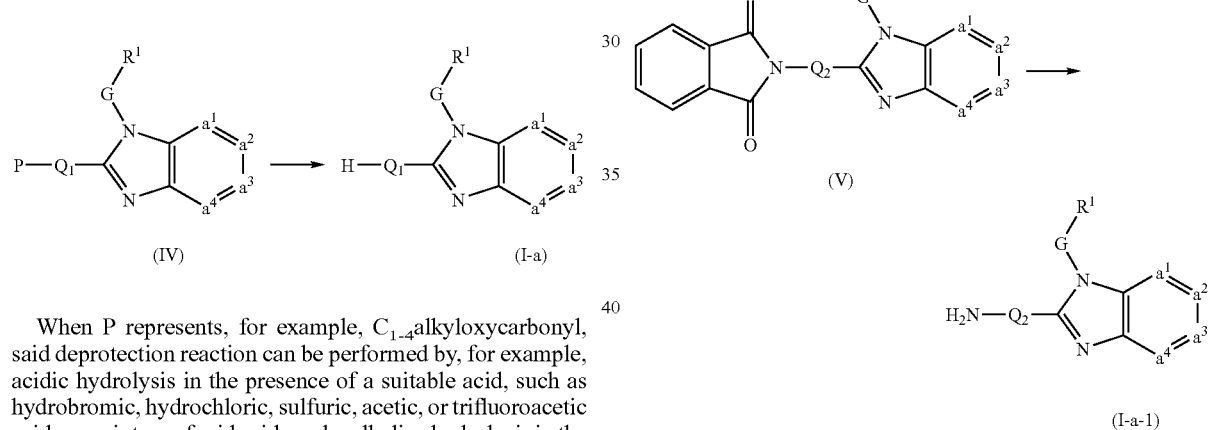

When P represents, for example, $C_{1-4}$alkyloxycarbonyl, said deprotection reaction can be performed by, for example, acidic hydrolysis in the presence of a suitable acid, such as hydrobromic, hydrochloric, sulfuric, acetic, or trifluoroacetic acid or a mixture of said acids, or by alkaline hydrolysis in the presence of a suitable base, such as, for example potassium hydroxide, in a suitable solvent such as water, alcohol, a mixture of water-alcohol, methylene chloride. Suitable alcohols are methanol, ethanol, 2-propanol, 1-butanol and the like. In order to enhance the rate of the reaction, it is advantageous to heat the reaction mixture, in particular up to the reflux temperature. Alternatively, when P represents, for example, benzyl, the deprotection reaction can be performed by catalytic hydrogenation in the presence of hydrogen and an appropriate catalyst in a reaction-inert solvent. A suitable catalyst in the above reaction is, for example, platinum-on-charcoal, palladium-on-charcoal, and the like. An appropriate reaction-inert solvent for said reaction is, for example, an alcohol, e.g. methanol, ethanol, 2-propanol and the like, an ester, e.g. ethylacetate and the like, an acid, e.g. acetic acid and the like.

The catalytic hydrogenation reaction described above can also be used to prepare a compound of formula (I-a) by deprotecting and reducing an intermediate of formula (IV) wherein $Q_1$ comprises an unsaturated bond, said $Q_1$ being represented by $Q_{1a}$(CH=CH), and said intermediate being represented by formula (IV-a).

Compounds of formula (I) wherein, in the definition of Q, both $R^6$ substituents are hydrogen or $R^2$ and $R^4$ are both hydrogen, said Q being represented by $H_2N$-$Q_2$, and said compounds being represented by formula (I-a-1), can also be prepared by deprotecting an intermediate of formula (V).

Said deprotection reaction can be performed in the presence of a suitable base such as, for example hydrazine, or in the presence of a suitable acid, such as hydrochloric acid and the like, in a suitable solvent, such as an alcohol, acetic acid and the like.

Compounds of formula (I-a-1) can also be prepared by deprotecting an intermediate of formula (VI) according to the procedure described for the preparation of compounds of formula (I-a).

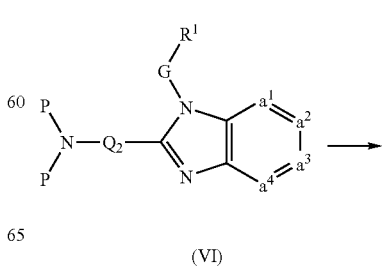

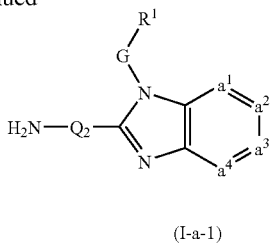

(I-a-1)

Compounds of formula (I-a) or (I-a-1), wherein $Q_1$ or $Q_2$ comprise a hydroxy substituent, said $Q_1$ or $Q_2$ being represented by $Q_{1'}(OH)$ or $Q_{2'}(OH)$, and said compounds being represented by formula (I-a-2) or (I-a-1-1), can be prepared by deprotecting an intermediate of formula (VII) or (VIII) as described hereinabove for the preparation of compounds of formula (I-a).

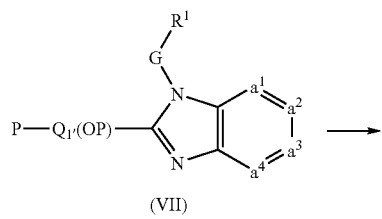

(VII)

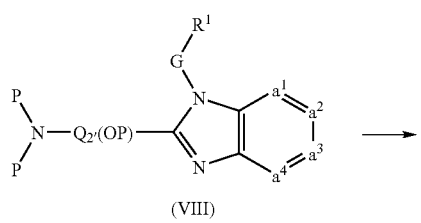

(I-a-2)

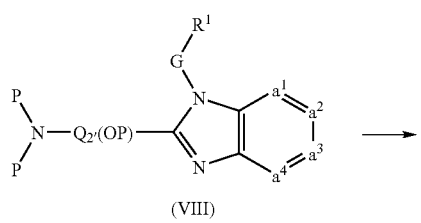

(VIII)

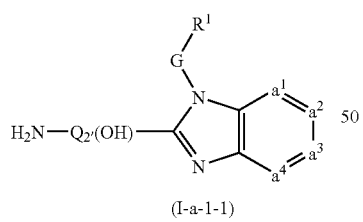

(I-a-1-1)

Compounds of formula (I) wherein, in the definition of Q, both $R^6$ substituents are hydrogen or $R^2$ and $R^4$ are both hydrogen, and the carbon adjacent to the nitrogen carrying the $R^6$, or $R^2$ and $R^4$ substituents contains at least one hydrogen, said Q being represented by $H_2N$-$Q_3H$, and said compounds being represented by formula (I-a-1-2) can also be obtained by reductive amination of intermediates of formula (IX) in the presence of a suitable amination reagent, such as, for example, ammonia, hydroxylamine, or benzylamine, and in the presence of a suitable reducing agent, e.g. hydrogen, and an appropriate catalyst. An appropriate catalyst in the above reaction is, for example, platinum-on-charcoal, palladium-on-charcoal, rhodium-on-$Al_2O_3$, and the like, optionally in the presence of a catalyst poison, such as a thiophene solution. A suitable reaction-inert solvent for the above reaction is, for example, an alcohol, e.g. methanol, ethanol, 2-propanol and the like.

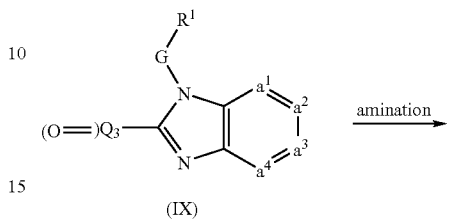

(IX)

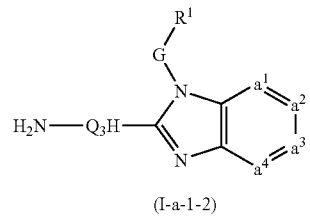

(I-a-1-2)

Compounds of formula (I), wherein Q comprises a —$CH_2NH_2$ moiety, said Q being represented by $H_2N$—$CH_2$-$Q_4$, and said compounds being represented by formula (I-a-1-3) can be prepared by reducing an intermediate of formula (X).

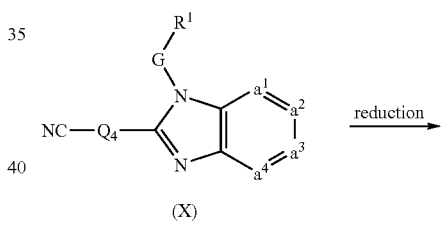

(X)

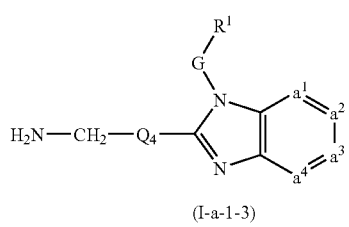

(I-a-1-3)

Said reduction can be performed with a suitable reducing agent, such as lithium aluminium hydride or hydrogen, optionally in the presence of a suitable catalyst, such as Raney Nickel. A suitable solvent for the above reaction is, for example, tetrahydrofuran, or a solution of ammonia in an alcohol. Suitable alcohols are methanol, ethanol, 2-propanol and the like. Said reduction reaction performed in a solution of ammonia in an alcohol can also be used to prepare compounds of formula (I-a-1-3), wherein $R^1$ is substituted with $C_{1-6}$alkyloxy$C_{1-6}$alkyl, said $R^1$ being represented by $R^{1'}$—$C_{1-6}$ alkyloxy$C_{1-6}$alkyl, and said compounds being represented by formula (I-a-1-3-1) starting from an intermediate of formula (X-a).

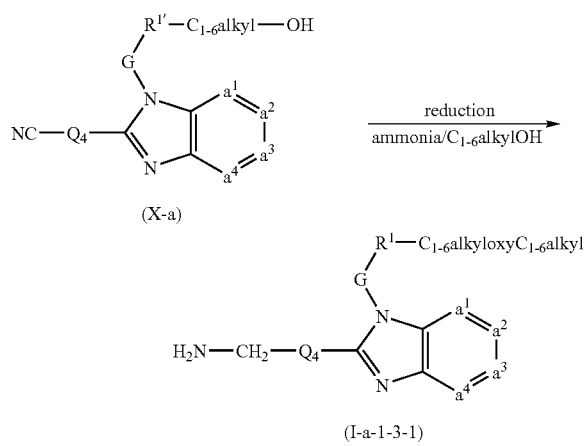

(X-a)

(I-a-1-3-1)

Compounds of formula (I), wherein Q comprises a —CH$_2$—CHOH—CH$_2$—NH$_2$ moiety, said Q being represented by H$_2$N—CH$_2$—CHOH—CH$_2$-Q$_4'$, and said compounds being represented by formula (I-a-1-3-2), can be prepared by reacting an intermediate of formula (XI) with ammonia in the presence of a suitable reaction-inert solvent, such as an alcohol, e.g. methanol.

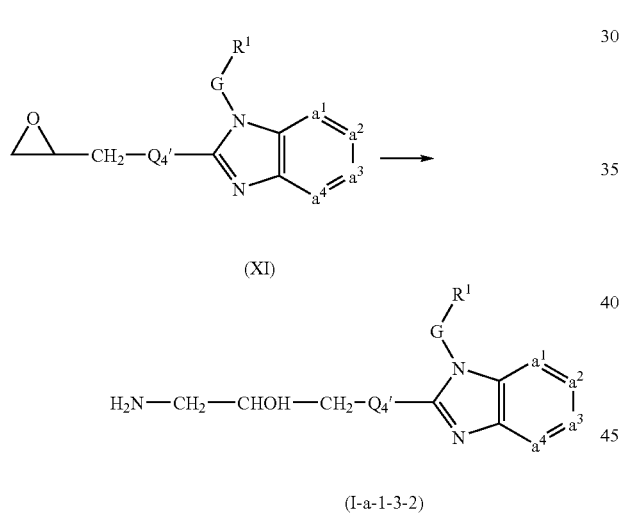

(XI)

(I-a-1-3-2)

Compounds of formula (I), wherein, in the definition of Q, R$^2$ or one R$^6$ substituent is formyl, said Q being represented by H—C(=O)-Q$^1$, and said compounds being represented by formula (I-b), can be prepared by reacting an intermediate of formula (XII) with formic acid, formamide and ammonia.

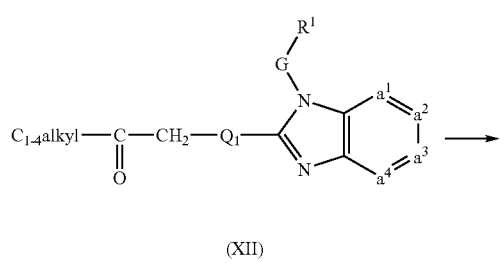

(XII)

-continued

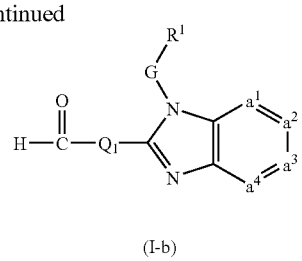

(I-b)

Compounds of formula (I), wherein, in the definition of Q, R$^2$ is other than hydrogen, said R$^2$ being represented by R$^{2a}$, R$^4$ is hydrogen, and the carbon atom adjacent to the nitrogen atom carrying the R$^2$ and R$^4$ substituents, carries also at least one hydrogen atom, said Q being represented by R$^{2a}$—NH—HQ$_5$, and said compounds being represented by formula (I-c), can be prepared by reductive amination of an intermediate of formula (XIII) with an intermediate of formula (XIV) in the presence of a suitable reducing agent, such as hydrogen, and a suitable catalyst, such as palladium-on-charcoal, platinum-on-charcoal, and the like. A suitable reaction-inert solvent for the above reaction is, for example, an alcohol, e.g. methanol, ethanol, 2-propanol and the like.

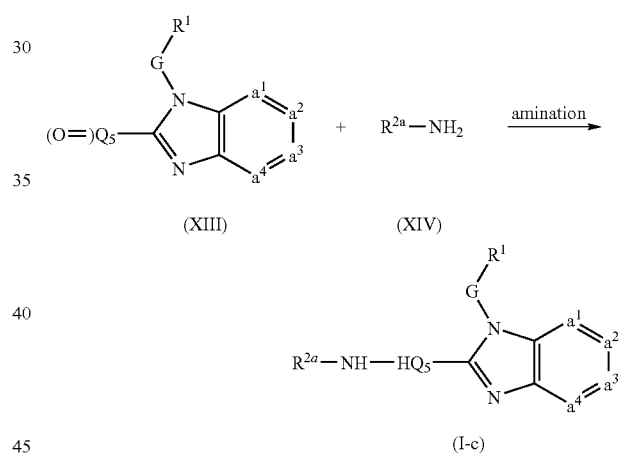

(XIII)         (XIV)

(I-c)

Compounds of formula (I-c), wherein R$^{2a}$ represents C$_{1-10}$alkyl substituted with N(R$^6$)$_2$ and with hydroxy, and the carbon atom carrying the hydroxy, carries also two hydrogen atoms, said R$^{2a}$ being represented by [(C$_{1-9}$alkyl)CH$_2$OH]—N(R$^6$)$_2$, and said compounds being represented by formula (I-c-1), can be prepared by reducing an intermediate of formula (XV) in the presence of a suitable reducing agent, such as lithium aluminium hydride, in a suitable reaction-inert solvent, such as tetrahydrofuran.

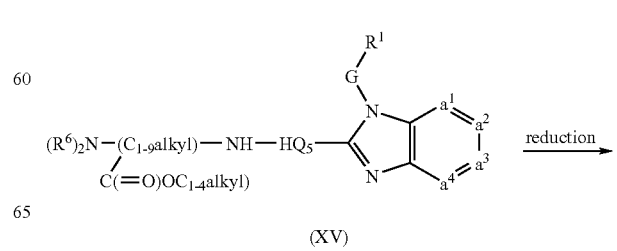

(XV)

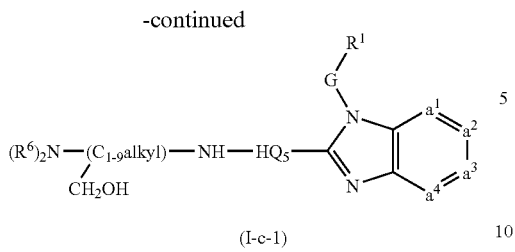

(I-c-1)

Compounds of formula (I) wherein, in the definition of Q, $R^2$ or one $R^6$ substituent is hydrogen, said Q being represented by H-$Q_1$, and wherein $R^1$ is aryl or a monocyclic heterocycle substituted with 1 or more substituents selected from hydroxy, hydroxy$C_{1-6}$alkyl, or HO(—$CH_2$—$CH_2$—O)$_n$—, said substituents being represented by formula A-OH, said $R^1$ being represented by $R^{1a}$-(A-OH)$_w$, with w being the amount of substituents on $R^{1a}$ ranging from 1 to 4, and said compounds being represented by formula (I-d), can be prepared by deprotecting an intermediate of formula (XVI) with a suitable acid, such as hydrochloric acid and the like, optionally in the presence of a suitable solvent, such as an alcohol. Suitable alcohols are methanol, ethanol, 2-propanol and the like.

Alternatively, one protecting group may also protect more than one substituent of $R^{1a}$, said protecting group being represented by $P_1$, as represented by formula (XVI-a). The two ways of protecting the substituents of $R^{1a}$, i.e. with a separate, as in formula (XVI), or a combined, as in formula (XVI-a), protecting group, may also be combined in the same intermediate, as represented by formula (XVI-b).

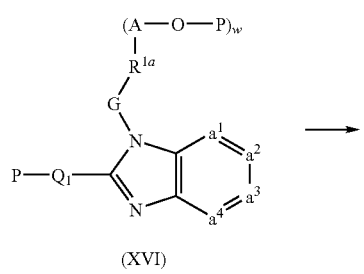

(XVI)

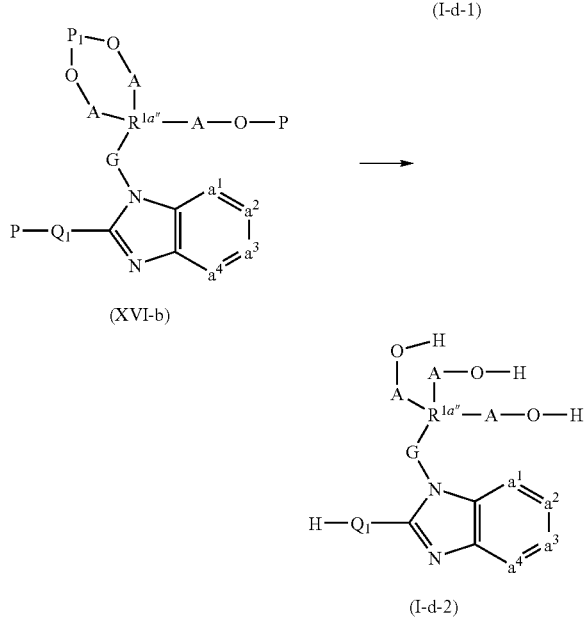

Compounds of formula (I), wherein Q is a radical of formula (b-2), said compounds being represented by formula (I-e), can be prepared by reacting an intermediate of formula (XVII) with an intermediate of formula (XVIII) in the presence of sodium cyanide and a suitable reaction-inert solvent, such as an alcohol, e.g. methanol and the like.

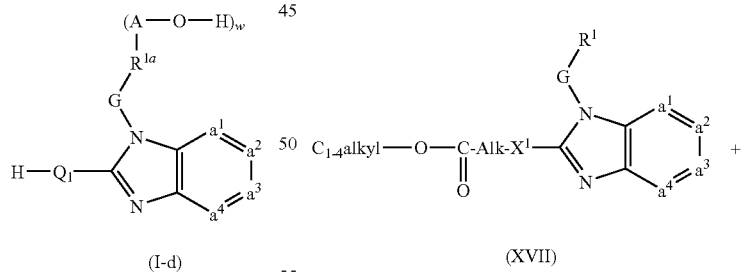

(XVII)

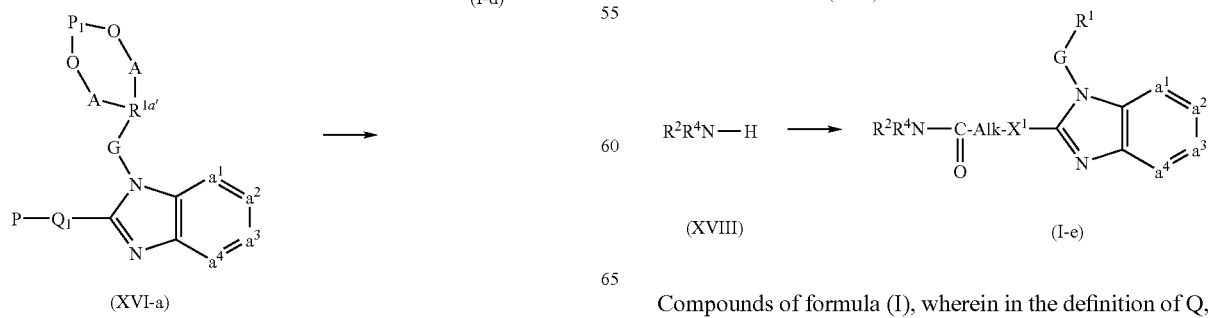

(XVIII)    (I-e)

Compounds of formula (I), wherein in the definition of Q, $X^2$ is $C_{2-4}$alkyl-$NR^4$, said Q being represented by $Q_6$N—

$CH_2$—$C_{1-3}$alkyl-$NR^4$, and said compounds being represented by formula (I-p), can be prepared by reacting an intermediate of formula (XIX) with an intermediate of formula (XX) in the presence of isopropyl titanate (IV) and a suitable reducing agent, such as $NaBH_3CN$, and in the presence of a suitable reaction-inert solvent, such as methylene chloride and an alcohol, e.g. ethanol.

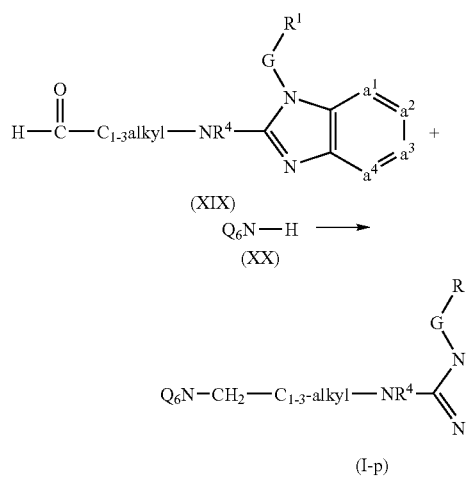

(XIX)

$Q_6N$—H ⟶

(XX)

$Q_6N$—$CH_2$—$C_{1-3}$-alkyl—$NR^4$ (I-p)

Compounds of formula (I-p), wherein $R^2$ is $C_{1-6}$alkylcarbonyl, and Q is a radical of formula (b-6), wherein $Y^1$ is $NR^2$, said compounds being represented by formula (I-p-1), can be prepared by reacting an intermediate of formula (XIX) with an intermediate of formula (XX-a) according to the procedure described for the preparation of a compound of formula (I-p).

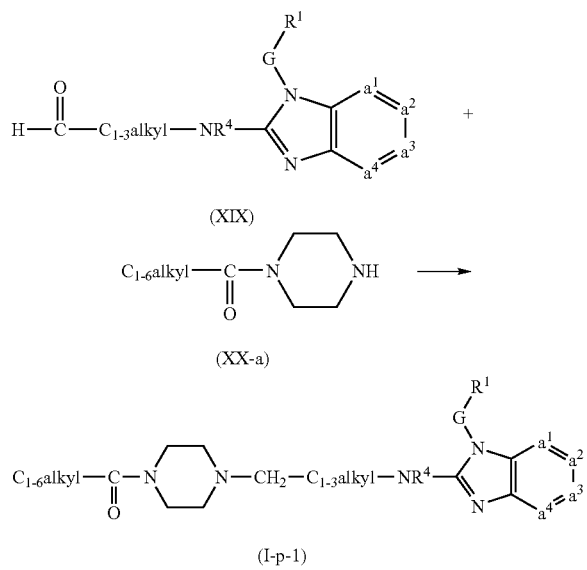

(XIX)

(XX-a)

(I-p-1)

Compounds of formula (I), wherein G is substituted with hydroxy or HO(—$CH_2CH_2O$)$_n$—, said G being represented by $G_1$-OH, and said compounds being represented by formula (I-q), may be prepared by deprotecting an intermediate of formula (XXI), wherein P represents a suitable protecting group, for example, benzyl. Said deprotection reaction can be performed by catalytic hydrogenation in the presence of hydrogen and an appropriate catalyst in a reaction-inert solvent. A suitable catalyst in the above reaction is, for example, platinum-on-charcoal, palladium-on-charcoal, and the like. An appropriate reaction-inert solvent for said reaction is, for example, an alcohol, e.g. methanol, ethanol, 2-propanol and the like, an ester, e.g. ethylacetate and the like, an acid, e.g. acetic acid and the like.

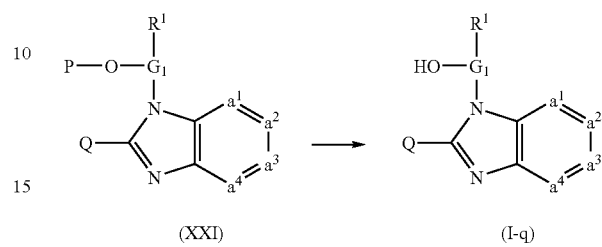

(XXI)    (I-q)

Compounds of formula (I), wherein G is substituted with hydroxy and the carbon atom carrying the hydroxy substituent carries also at least one hydrogen, said G being represented by H-$G_2$-OH, and said compounds being represented by formula (I-q-1), can also be prepared by reducing an intermediate of formula (XXII).

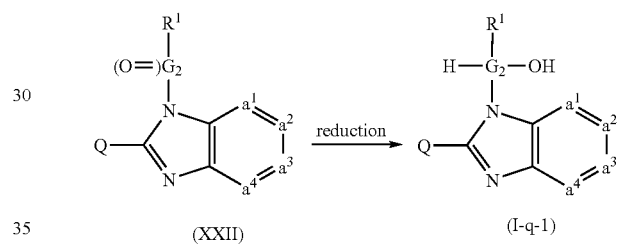

(XXII)    (I-q-1)

Said reduction reaction can be performed in the presence of a suitable reducing agent, such as, for example sodium borohydride, in a reaction-inert solvent, such as an alcohol or tetrahydrofuran or a mixture thereof. Suitable alcohols are methanol, ethanol, 2-propanol and the like.

Compounds of formula (I) may be converted into each other following art-known functional group transformation reactions, comprising those described hereinafter.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I), wherein $R^1$ is monocyclic heterocycle substituted with $C_{1-6}$alkyloxycarbonyl, said $R^1$ being represented by $R^{1'}$—C(=O)O$C_{1-6}$alkyl, and said compounds being represented by formula (I-f), can be prepared by esterification of a compound of formula (I-g) in the presence of a suitable alcohol, e.g. methanol, ethanol, propanol, butanol, pentanol, hexanol and the like, and in the presence of a suitable acid, such as hydrochloric acid and the like.

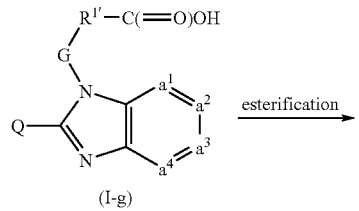

(I-g)

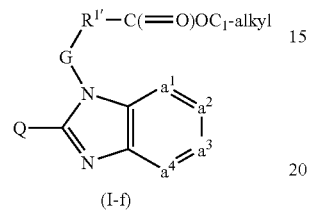

(I-f)

Compounds of formula (I-a) may be converted into compounds of formula (I) wherein, in the definition of Q, $R^2$ or at least one $R^6$ substituent is other than hydrogen, said $R^2$ or $R^6$ being represented by $Z_1$, said Q being represented by $Z_1$-$Q_1$, and said compounds being represented by formula (I-h), by reaction with a reagent of formula (XXIII), wherein $W_2$ is a suitable leaving group, such as a halo atom, e.g. bromo, or 4-methylbenzenesulphonate, in the presence of a suitable base, such as, for example disodium carbonate, dipotassium carbonate, sodium hydroxide and the like, in a reaction-inert solvent, e.g. 3-methyl-2-butanone, acetonitrile, N,N-dimethylformamide.

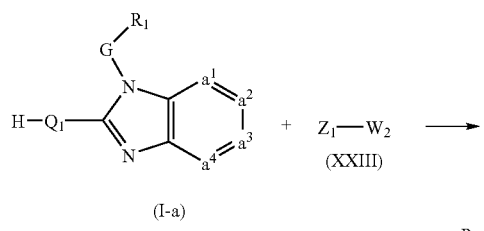

(I-a)   (XXIII)

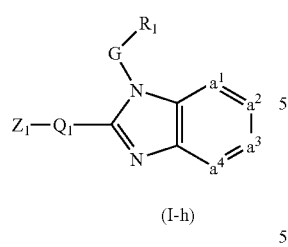

(I-h)

Compounds of formula (I-h), wherein, in the definition of $Z_1$, $R^2$ is $CH_2$—$C_{1-9}$alkyl substituted with $N(R^6)_2$, said compounds being represented by formula (I-h-1), can also be prepared by reacting a compound of formula (I-a) wherein, in the definition of H-$Q_1$, $R^2$ is hydrogen, said H-$Q_1$ being represented by H-$Q_{1b}$, and said compounds being represented by formula (I-a-3), with an intermediate of formula (XXIV), in the presence of a suitable reducing agent, such as sodium cyanoborohydride, in a suitable reaction-inert solvent, such as an alcohol.

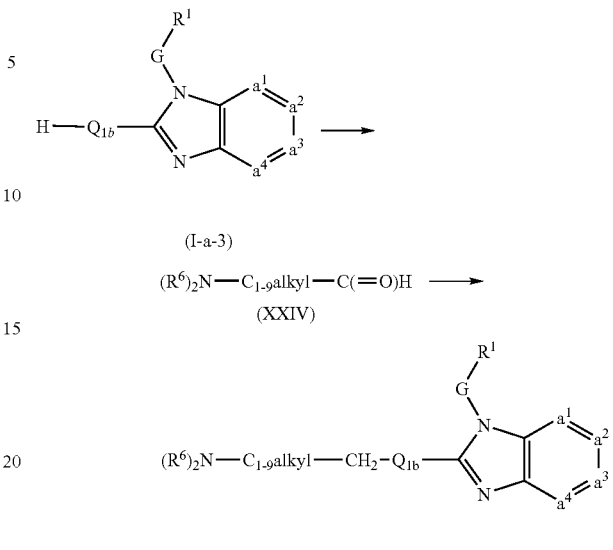

(I-a-3)

$(R^6)_2N$—$C_{1-9}$alkyl—$C(=O)H$ ⟶
(XXIV)

(I-h-1)

Compounds of formula (I-h), wherein $Z_1$ comprises formyl, $C_{1-6}$alkylcarbonyl, Hetcarbonyl or $C_{1-6}$alkyloxycarbonyl, said $Z_1$ being represented by $Z_{1a}$, and said compounds being represented by formula (I-h-2), can be converted into compounds of formula (I-a), by acidic hydrolysis in the presence of a suitable acid, such as hydrobromic, hydrochloric, sulfuric, acetic, or trifluoroacetic acid or a mixture of said acids, or by alkaline hydrolysis in the presence of a suitable base, such as, for example potassium hydroxide, in a suitable solvent such as water, alcohol, a mixture of water-alcohol, methylene chloride. Suitable alcohols are methanol, ethanol, 2-propanol, 1-butanol, sec. butanol and the like. In order to enhance the rate of the reaction, it is advantageous to work at elevated temperatures.

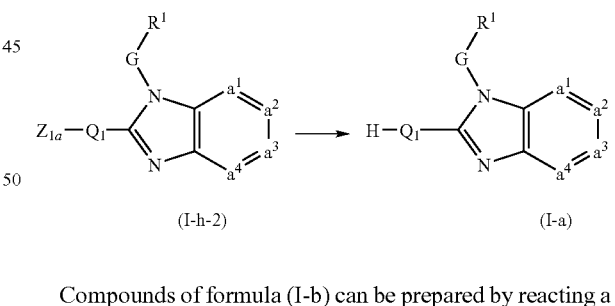

(I-h-2)                    (I-a)

Compounds of formula (I-b) can be prepared by reacting a compound of formula (I-a) with formic acid.

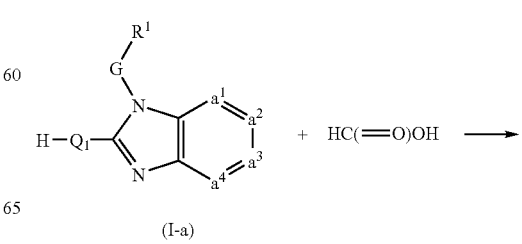

(I-a)

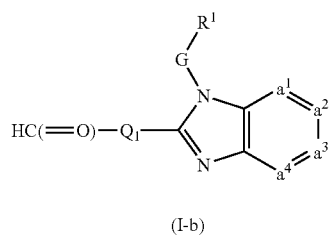

(I-b)

Compounds of formula (I) wherein $R^1$ is monocyclic heterocycle or aryl substituted with hydroxy, said $R^1$ being represented by HO—$R^{1'}$, and said compounds being represented by formula (I-i), can be prepared by deprotecting a compound of formula (I-j), wherein $R^1$ is monocyclic heterocycle or aryl substituted with $C_{1-6}$alkyloxy or aryl$C_{1-6}$alkyloxy, said $C_{1-6}$alkyl or aryl$C_{1-6}$alkyl being represented by $Z_2$, and said $R^1$ being represented by $Z_2$-O—$R^{1'}$. Said deprotection can be performed in a reaction-inert solvent, such as, for example methylene chloride, in the presence of a suitable deprotecting agent, e.g. tribromoborane.

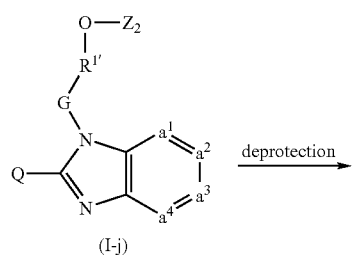

(I-j)

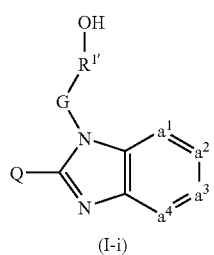

(I-i)

Compounds of formula (I) wherein $R^1$ is monocyclic heterocycle substituted with halo(—$CH_2$—$CH_2$—O)$_n$, said compounds being represented by formula (I-k), can be converted into compounds of formula (I-1-1) or (I-1-2) by reaction with an appropriate amine of formula (XXV) or (XXVI) in a suitable reaction-inert solvent, e.g. tetrahydrofuran.

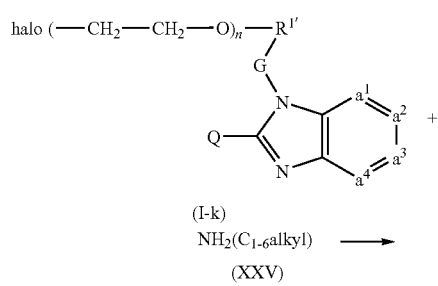

(I-k)

$NH_2(C_{1-6}alkyl)$ ⟶

(XXV)

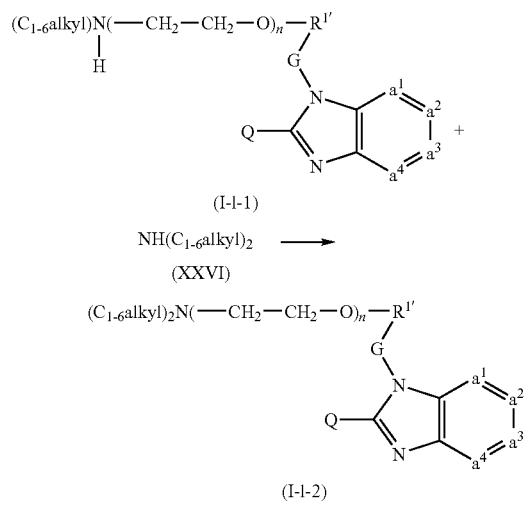

(I-l-1)

$NH(C_{1-6}alkyl)_2$ ⟶

(XXVI)

(I-l-2)

Compounds of formula (I) wherein $R^1$ is monocyclic heterocycle or aryl substituted with halo, said compounds being represented by formula (I-m) can be converted into compounds of formula (I) by reaction with 1-butanethiol in the presence of palladium-on-charcoal and CaO in a suitable reaction-inert solvent, such as tetrahydrofuran.

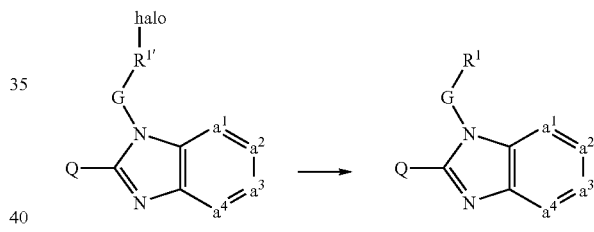

(I-m)   (I)

Compounds of formula (I) wherein a hydrogen atom in the radicals of formula (a-1), (a-2), (a-3), (a-4) or (a-5) is replaced by nitro, said compounds being represented by formula (I-n) may be reduced to a compound of formula (I-o) in the presence of a suitable reducing agent, such as hydrogen, optionally in the presence of a suitable catalyst, such as platinum-on-charcoal, and optionally in the presence of a suitable catalyst poison, e.g. a thiophene solution. The reaction may be performed in a suitable reaction-inert solvent, such as an alcohol.

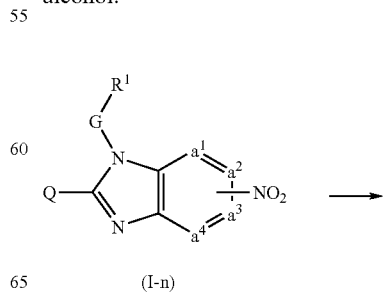

(I-n)

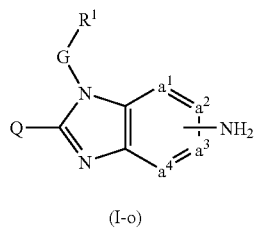

(I-o)

In the following paragraphs, there are described several methods of preparing the intermediates in the foregoing preparations. A number of intermediates and starting materials are commercially available or are known compounds which may be prepared according to conventional reaction procedures generally known in the art or analogous to the procedures described in EP-A-0005318, EP-A-0099139, EP-A-0151824, EP-A-0151826, EP-A-0232937, EP-A-0295742, EP-A-0297661, EP-A-0539420, EP-A-0539421, U.S. Pat. No. 4,634,704, U.S. Pat. No. 4,695,569.

In the foregoing and the following preparations, the reaction mixture is worked up following art-known methods and the reaction product is isolated and, if necessary, further purified.

Intermediates of formula (III) can be prepared by reacting an intermediate of formula (XXVII) with a suitable leaving group, i.e. $W_1$, introducing agent, e.g. 1-halo-2,5-pyrrolidinedione in the presence of dibenzoyl peroxide, in a reaction-inert solvent, e.g. tetrachloromethane.

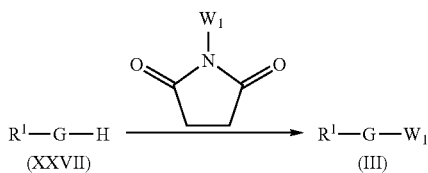

Intermediates of formula (XXVII), wherein $R^1$ is monocyclic heterocycle or aryl substituted with chloro, said $R^1$ being represented by Cl—$R^{1'}$ and said intermediates being represented by formula (XXVII-a) can be prepared by reacting an intermediate of formula (XXVIII), wherein (O=)$R^{1b}$H is defined as a carbonyl derivative of $R^{1'}$ wherein one carbon or nitrogen, adjacent to the carbonyl, carries at least one hydrogen, with phosphorus oxychloride. Intermediates of formula (XXVIII) may also react as their enol tautomeric forms.

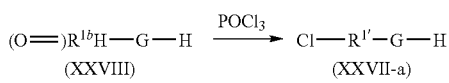

Intermediates of formula (III) wherein $W_1$ is chloro, which is attached to a carbon atom carrying at least one hydrogen, said G being represented by $G_3H$, and said intermediates being represented by formula (III-a) can also be prepared by reacting an intermediate of formula (XXIX) with thionylchloride in a reaction-inert solvent, e.g. methylenechloride.

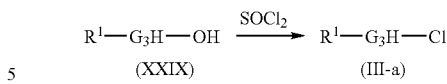

Intermediates of formula (XXIX) can be prepared by reducing an intermediate of formula (XXX) in a reaction-inert solvent, e.g. an alcohol, in the presence of a suitable reducing agent, e.g. sodium borohydride.

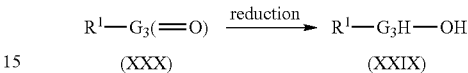

Alternatively, intermediates of formula (XXIX) can also be prepared by deprotecting an intermediate of formula (XXXI), wherein P is a suitable protecting group, e.g. $C_{1-4}$alkylcarbonyl, in a reaction-inert solvent, such as an alcohol, in the presence of a suitable base, e.g. sodium hydroxide.

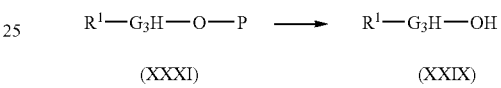

Intermediates of formula (XXX), wherein $G_3$(=O) is CH(=O), said intermediates being represented by formula (XXX-a), can be prepared by reacting an intermediate of formula (XXXII), wherein $W_3$ is a suitable leaving group, such as a halo atom, e.g. bromo, with N,N-dimethylformamide in the presence of butyllithium in a reaction-inert solvent, e.g. tetrahydrofuran, diethylether or a mixture thereof.

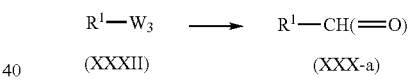

Intermediates of formula (IV) can be prepared by reacting an intermediate of formula (XXXIII-a) or (XXXIII-b), wherein P represents a suitable protecting group, such as, for example, $C_{1-4}$alkyloxycarbonyl, with an intermediate of formula (III) according to the reaction described for the general preparation of compounds of formula (I).

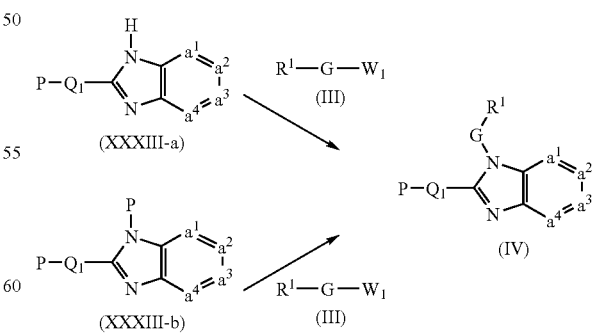

Intermediates of formula (IV) can also be prepared by reacting an intermediate of formula (XXXIII-a) with an intermediate of formula (XXXIV) that has reacted with methanesulfonyl chloride, in the presence of a suitable base, such as sodium hydride, and in the presence of a suitable reaction-inert solvent, e.g. N,N-dimethylformamide.

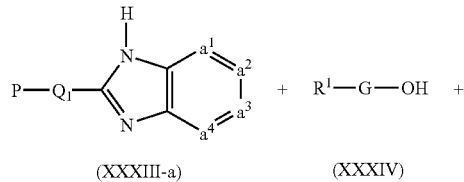

(XXXIII-a)    (XXXIV)

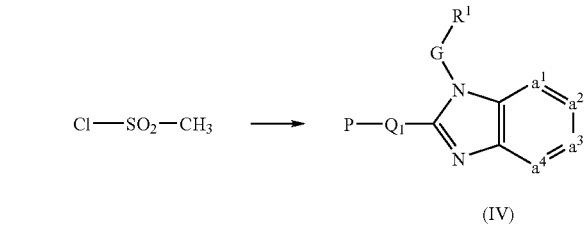

(IV)

Intermediates of formula (IV) can also be prepared by a cyclization reaction of an intermediate of formula (XXXV) in a reaction-inert solvent, e.g. an alcohol or N,N-dimethylformamide, in the presence of mercury oxide and sulphur.

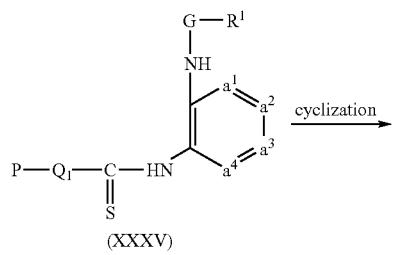

(XXXV)

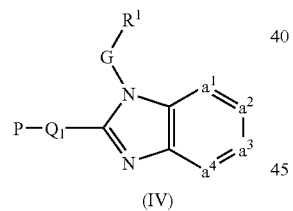

(IV)

Intermediates of formula (IV) wherein $Q_1$ comprises an unsaturated bond, said $Q_1$ being represented by $Q_{1a}$(CH=CH), and said intermediates by formula (IV-a), can be prepared by reacting an intermediate of formula (XXXVI) with an intermediate of formula (III) in the presence of a suitable base, such as dipotassium carbonate.

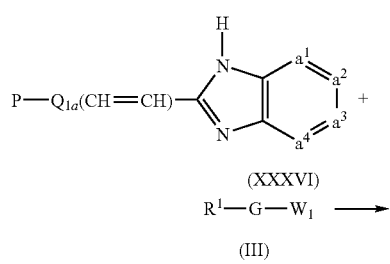

(XXXVI)

$R^1$—G—$W_1$ (III)

-continued

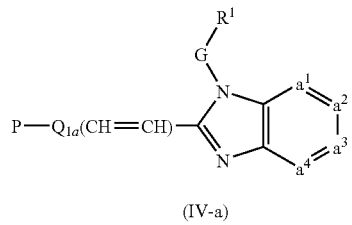

(IV-a)

Intermediates of formula (IV) wherein, in the definition of $Q_1$, the $X^1$ or $X^2$ moieties in the radicals of formula (b-1) to (b-8) represent NH, said $Q_1$ being represented by $Q_{1c}$-NH, and said intermediates by formula (IV-b), may also be prepared by reacting an intermediate of formula (XXXVII) with an intermediate of formula (XXXVIII).

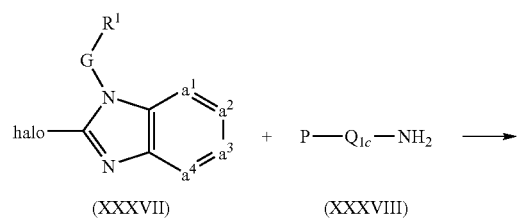

(XXXVII)    (XXXVIII)

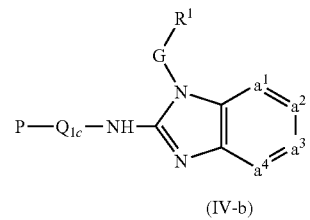

(IV-b)

Intermediates of formula (IV) wherein $R^1$ is monocyclic heterocycle substituted with amino or mono- or di($C_{1-6}$alkyl) amino, said $R^1$ being represented by $R^{5a}R^{5b}N$—$R^{1'}$, wherein $R^{5a}$ and $R^{5b}$ are defined as described above, and said intermediates being represented by formula (IV-c), can be prepared by reacting an intermediate of formula (XXXIX) with an appropriate amine, represented by formula (XL), in the presence of an appropriate catalyst, e.g. palladium, and (R)-(+)-2,2'-bis(diphenyl-phosphino)-1,1'-binaphtyl, in a suitable reaction-inert solvent, e.g. tetrahydrofuran.

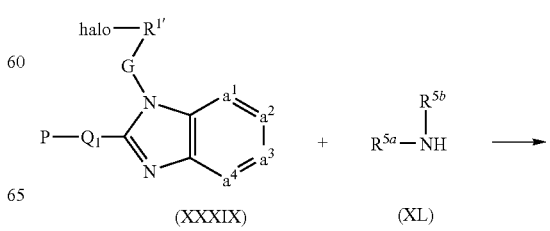

(XXXIX)    (XL)

(IV-c)

Intermediates of formula (IV) wherein $R^1$ is monocyclic heterocycle substituted with $C(=O)-NR^{5a}R^{5b}$, wherein $R^{5a}$ and $R^{5b}$ are defined as described above, said $R^1$ being represented by $R^{5a}R^{5b}N-C(=O)-R^{1'}$, and said intermediates being represented by formula (IV-d), can be prepared by reacting an intermediate of formula (XXXIX) with an appropriate amine, represented by formula (XL), under an atmosphere of carbon monoxide, in the presence of a suitable catalyst, e.g. palladium (II) acetate, and 1,3-bis(diphenylphosphino)propane, in a suitable reaction-inert solvent, e.g. tetrahydrofuran.

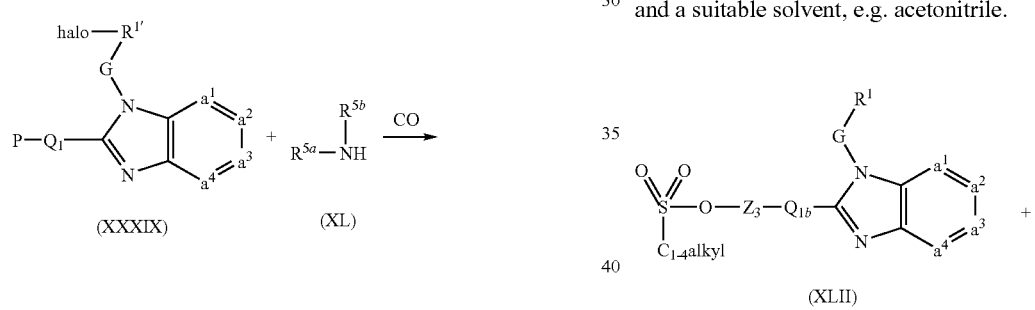

(XXXIX)   (XL)

(IV-d)

Intermediates of formula (IV) wherein $P-Q_1$ comprises $C_{1-10}$alkyl or $C_{3-7}$cycloalkyl substituted with $NR^6-P$, said $C_{1-10}$alkyl or $C_{3-7}$cycloalkyl being represented by $Z_3$, said $P-Q_1$ being represented by $P-NR^6-Z_3-Q_{1b}$, and said intermediates being represented by formula (IV-e), can be prepared by reacting a compound of formula (I-a-3) with an intermediate of formula (XLI), wherein $W_4$ represents a suitable leaving group, such as p-toluenesulphonate. Said reaction can be performed in a reaction-inert solvent, e.g. acetonitrile, in the presence of a suitable base, e.g. dipotassium carbonate.

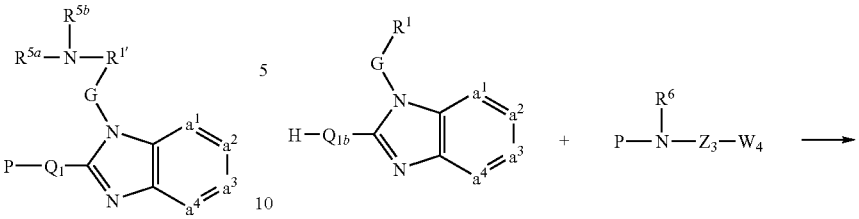

(I-a-3)   (XLI)

(IV-e)

Intermediates of formula (IV-e), wherein $R^6$ is hydroxy$C_{1-6}$ alkyl, said intermediates being represented by formula (IV-e-1), can be prepared by reacting an intermediate of formula (XLII) with an intermediate of formula (XLIII) in the presence of a suitable base, e.g. dipotassium carbonate, and a suitable solvent, e.g. acetonitrile.

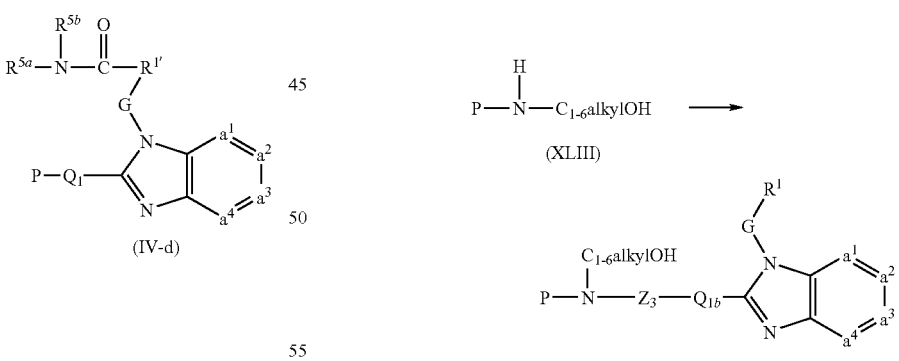

(XLII)

(XLIII)

(IV-e-1)

Intermediates of formula (XXXIII-a) or (XXXIII-b) can be prepared by protecting an intermediate of formula (XLIV) with a suitable protecting group, such as, for example, $C_{1-4}$alkyloxycarbonyl, in a reaction-inert solvent, such as methylene chloride or an alcohol, e.g. methanol, ethanol, 2-propanol and the like, in the presence of a suitable reagent, e.g. di $C_{1-4}$alkyl dicarbonate and optionally in the presence of a suitable base, e.g. sodium acetate.

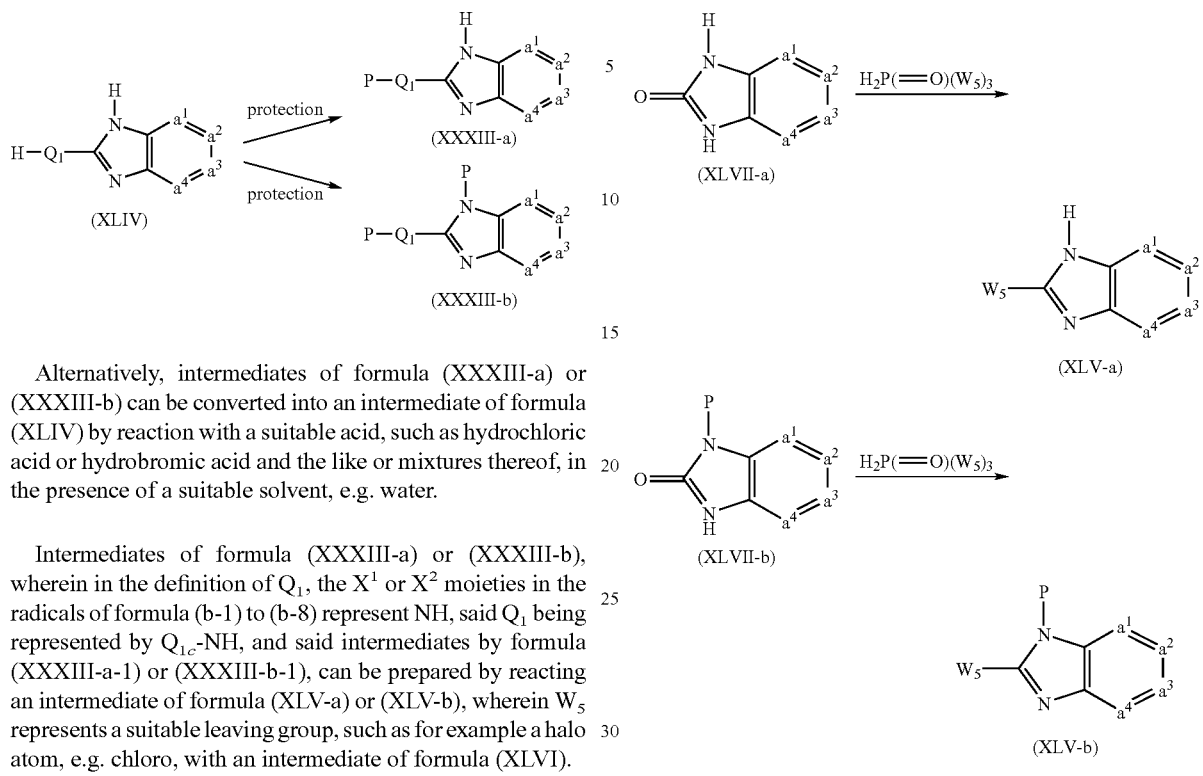

Alternatively, intermediates of formula (XXXIII-a) or (XXXIII-b) can be converted into an intermediate of formula (XLIV) by reaction with a suitable acid, such as hydrochloric acid or hydrobromic acid and the like or mixtures thereof, in the presence of a suitable solvent, e.g. water.

Intermediates of formula (XXXIII-a) or (XXXIII-b), wherein in the definition of $Q_1$, the $X^1$ or $X^2$ moieties in the radicals of formula (b-1) to (b-8) represent NH, said $Q_1$ being represented by $Q_{1c}$-NH, and said intermediates by formula (XXXIII-a-1) or (XXXIII-b-1), can be prepared by reacting an intermediate of formula (XLV-a) or (XLV-b), wherein $W_5$ represents a suitable leaving group, such as for example a halo atom, e.g. chloro, with an intermediate of formula (XLVI).

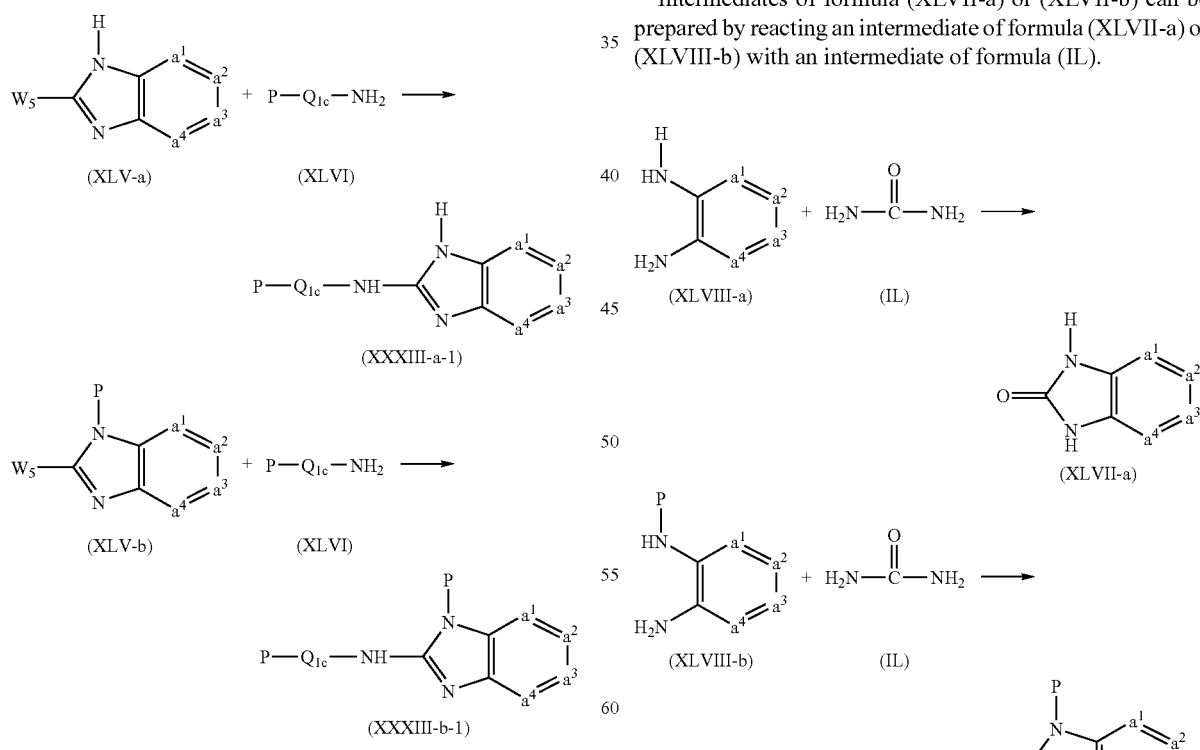

Intermediates of formula (XLV-a) or (XLV-b) can be prepared by reacting an intermediate of formula (XLVII-a) or (XLVII-b) with $H_2P(=O)(W_5)_3$ in the presence of a suitable acid, e.g. hydrochloric acid.

Intermediates of formula (XLVII-a) or (XLVII-b) can be prepared by reacting an intermediate of formula (XLVII-a) or (XLVIII-b) with an intermediate of formula (IL).

Intermediates of formula (XXXIII-a) can also be prepared by reacting an intermediate of formula (XLVIII-a) with P-Q$_1$-C(=NH)—O—CH$_2$—CH$_3$ in a reaction-inert solvent, such as an alcohol.

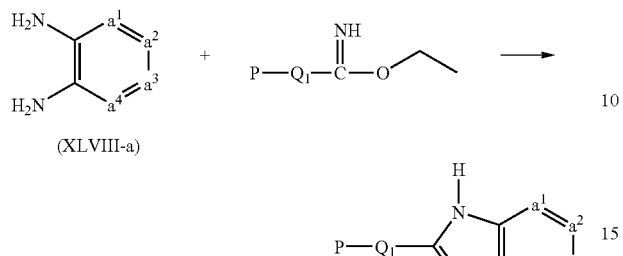

Intermediates of formula (XXXV) can be prepared by reacting an intermediate of formula (L) with an intermediate of formula P-Q$_1$=C=S, which is synthesized according to the procedures described in EP 0005318, in a reaction-inert solvent, such as an alcohol, e.g. ethanol. To increase the reaction rate, the reaction may be performed at elevated temperatures.

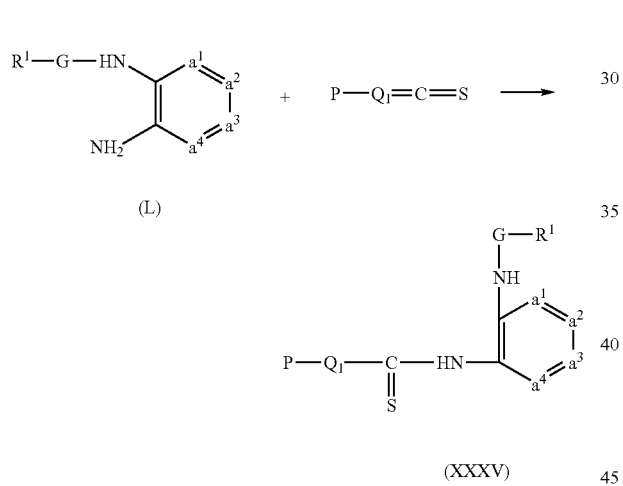

Intermediates of formula (L) can be obtained by reducing an intermediate of formula (LI) in a reaction-inert solvent, e.g. an alcohol, in the presence of a suitable reducing agent, e.g. hydrogen, and an appropriate catalyst, e.g. Raney Nickel.

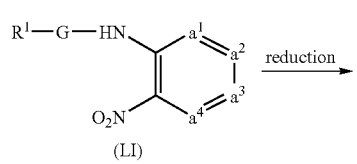

Intermediates of formula (LI) can be prepared by reacting an intermediate of formula (LII) with an intermediate of formula (LIII), in which W$_6$ represents a suitable leaving group, such as a halo atom, e.g. chloro. This reaction may be performed in a reaction-inert solvent, e.g. acetonitrile, in the presence of a suitable base, e.g. dipotassium carbonate.

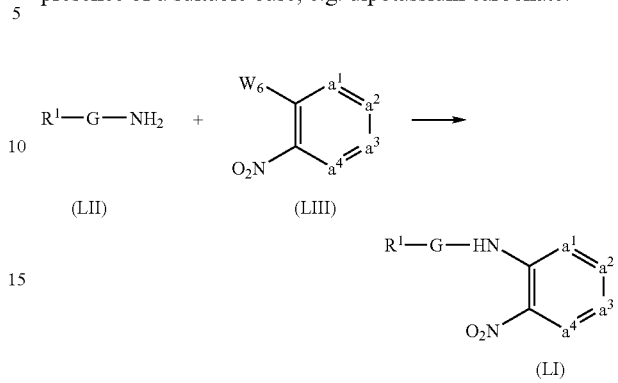

Intermediates of formula (LII) can be prepared by reacting an intermediate of formula (LIV) with a suitable acid, such as hydrochloric acid, in the presence of a suitable solvent, e.g. an alcohol, e.g. ethanol.

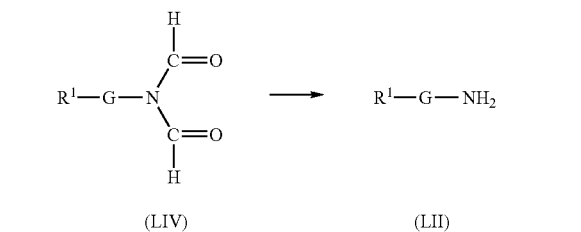

Intermediates of formula (LIV) can be prepared by reacting an intermediate of formula (III) with NaN[C(=O)H]$_2$.

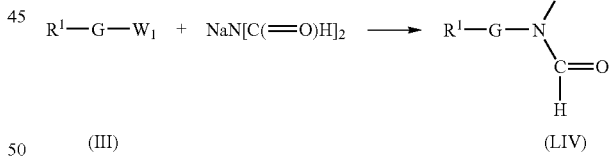

Intermediates of formula (LI) can also be prepared by reacting an intermediate of formula (LIII) with an intermediate of formula (LV) (J. Org. Chem., 25, p 1138, 1960) in a reaction-inert solvent, e.g. N,N-dimethylformamide, in the presence of an appropriate base, e.g. sodium hydride.

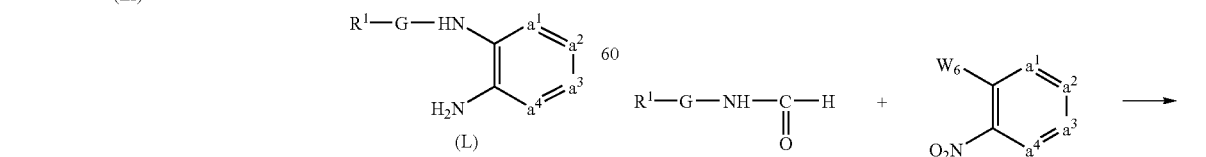

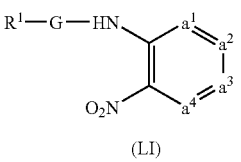

(LI)

Intermediates of formula (XXXVI) can be prepared by dehydrating an intermediate of formula (LVI) with a suitable acid, such as sulfuric acid.

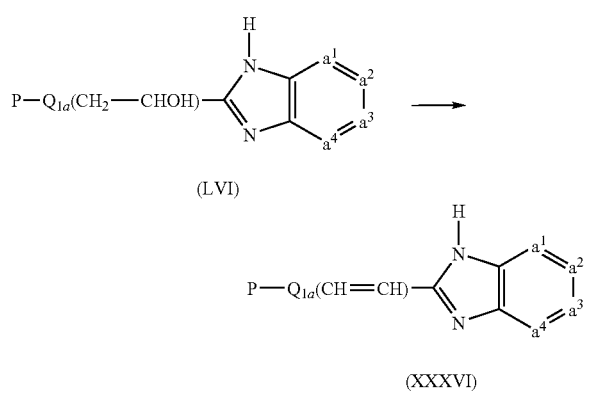

Intermediates of formula (LVI) wherein, in the definition of $Q_{1a}$, the $X^1$ or $X^2$ moieties are $CH_2$, said $Q_{1a}$ being represented by $Q_{1a'}$, and said intermediates being represented by formula (LVI-a), can be prepared by reacting a carbonyl moiety of formula (LVII) with an intermediate of formula (LVIII) in the presence of N,N-diisopropylamine and butyl lithium, in a suitable reaction-inert solvent, e.g. tetrahydrofuran.

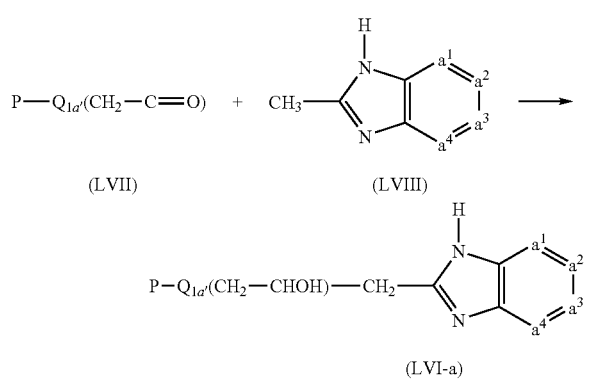

Intermediates of formula (IV), wherein G is $C_{1-10}$alkanediyl substituted with $C_{1-6}$alkyloxy, aryl$C_{1-6}$alkyloxy, $HO(-CH_2CH_2O)_n-$, $C_{1-6}$alkyloxy$(-CH_2CH_2O)_n-$, or aryl$C_{1-6}$alkyloxy$(-CH_2CH_2O)_n-$, said group of substituents being represented by O-$Z_4$, said G being represented by $Z_4$-O-$G_1$, and said intermediates being represented by formula (IV-f), can be prepared by reacting an intermediate of formula (XXXIII-a), with an intermediate of formula (LIX), optionally in the presence of a suitable acid, such as p-toluenesulfonic acid and the like, and optionally in the presence of a suitable solvent, such as N,N-dimethylacetamide. To increase the reaction rate, the reaction may be carried out at elevated temperatures.

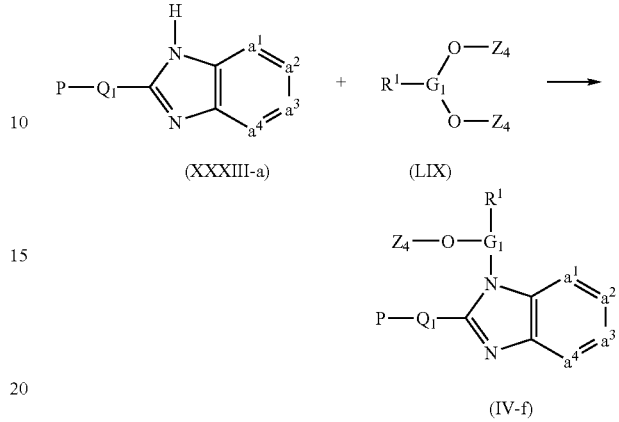

Intermediates of formula (LIX) can be prepared by reacting an intermediate of formula (LX) with a reagent of formula (LXI) or (LXII) in a reaction-inert solvent, such as an alcohol, or toluene, in the presence of an acid, e.g. 4-methylbenzenesulphonic acid.

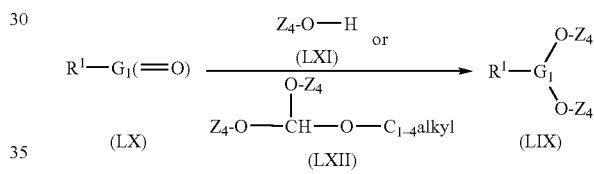

Intermediates of formula (LX) can be prepared by oxidizing an intermediate of formula (LXIII) with a suitable oxidizing agent, e.g. $MnO_2$, in a reaction-inert solvent, such as methylene chloride.

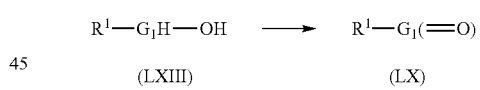

Intermediates of formula (IV-f) can also be prepared by reacting an intermediate of formula (IV) wherein G is $C_{1-10}$alkanediyl substituted with hydroxy, said G being represented by $G_1$-OH, and said intermediates being represented by formula (IV-g), with an intermediate of formula (LXIV), wherein $W_7$ is a suitable leaving group, such as a halo atom, e.g. iodo, in the presence of a suitable base, e.g. sodium hydride, in a reaction-inert solvent, e.g. tetrahydrofuran.

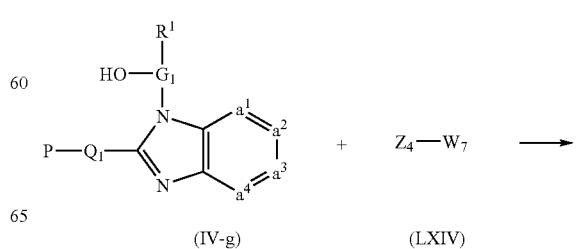

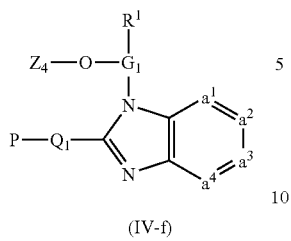

(IV-f)

Intermediates of formula (IV-g), wherein the carbon atom of $G_1$ carrying the hydroxy, also carries a hydrogen atom, said $G_1$-OH being represented by H-$G_2$-OH, and said intermediates being represented by formula (IV-g-1), can be prepared by reducing an intermediate of formula (LXV) in the presence of a suitable reducing agent, e.g. sodium borohydride, in a reaction-inert solvent, such as an alcohol, tetrahydrofuran or a mixture thereof. Intermediates of formula (LXV) can also first be deprotected, e.g. in the presence of a suitable acid, such as hydrochloric acid and the like, resulting in intermediates of formula (LXVI), followed by a reduction, resulting in a compound of formula (I-q-1) wherein Q represents H-$Q_1$, said compounds being represented by formula (I-q-1-1).

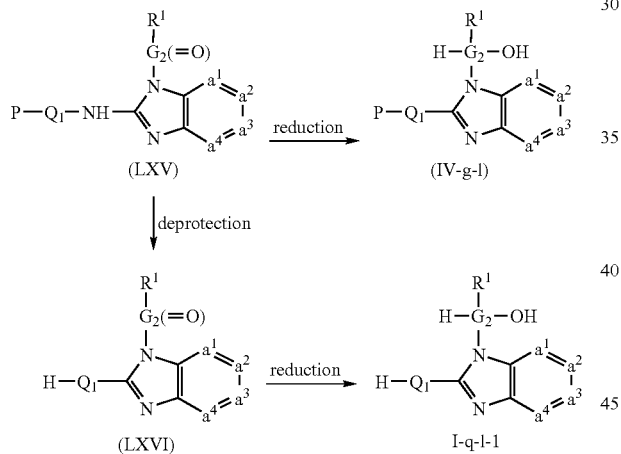

Intermediates of formula (IV), wherein G is ethyl substituted with hydroxy, said intermediates being represented by formula (IV-g-2) can also be prepared by reacting an intermediate of formula (XXXIII-a) with an intermediate of formula (LXVII) in the presence of a suitable base, such as sodium hydride, in a reaction-inert solvent, such as N,N-dimethylformamide.

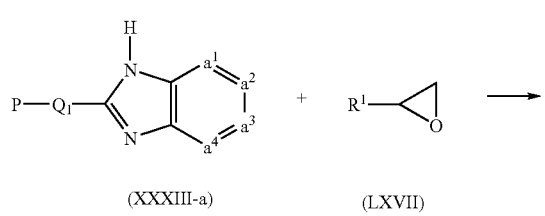

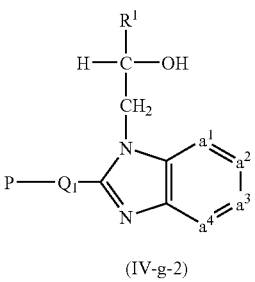

(IV-g-2)

A subgroup of intermediates of formula (IV-g-2), represented by formula (IV-g-2-1), can also be prepared by reacting an intermediate of formula (LXVIII) with an intermediate of formula (LXIX) in the presence of 1,3-dicyclohexylcarbodiimide, in a reaction-inert solvent, e.g. toluene.

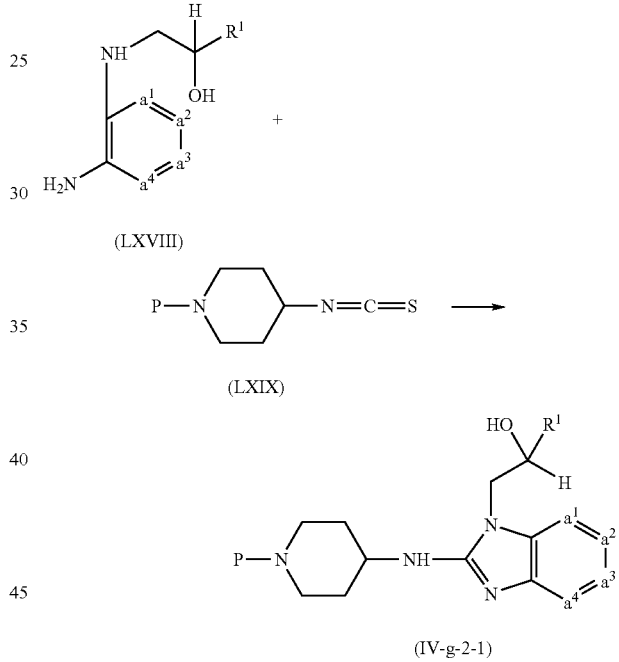

Intermediates of formula (LXV) can be prepared by reacting an intermediate of formula (XXXIII-a) with an intermediate of formula (LXX), wherein $W_8$ is a suitable leaving group, such as a halo atom, e.g. bromo, in the presence of a suitable base, e.g. sodium hydride, in a reaction-inert solvent, e.g. N,N-dimethylformamide.

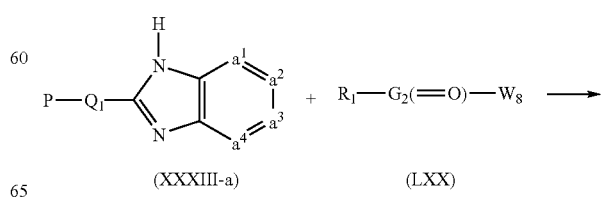

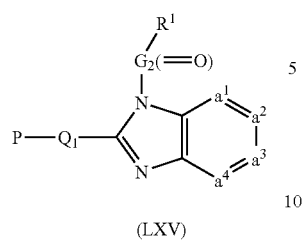

(LXV)

Intermediates of formula (V) can be prepared by reacting an intermediate of formula (LXXI) with 1H-isoindole-1,3 (2H)-dione in the presence of triphenylphosphine and diethyl azodicarboxylate.

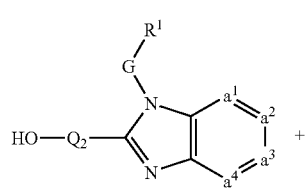

(LXXI)

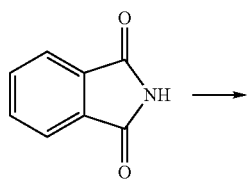

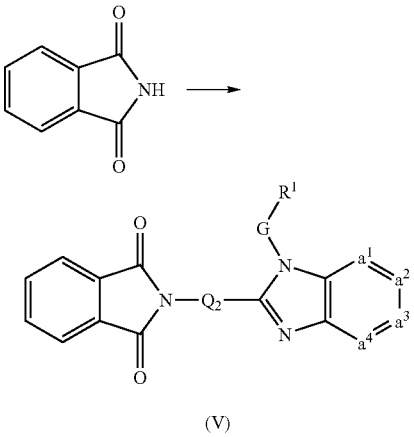

(V)

Intermediates of formula (LXXII) can be prepared by reacting an intermediate of formula (LXXI) with an intermediate of formula (LXXIII), wherein $W_9$ represents a suitable leaving group, such as a halo atom, e.g. chloro, in the presence of a suitable base, such as N,N-diethyl-ethanamine, and a suitable solvent, such as methylene chloride.

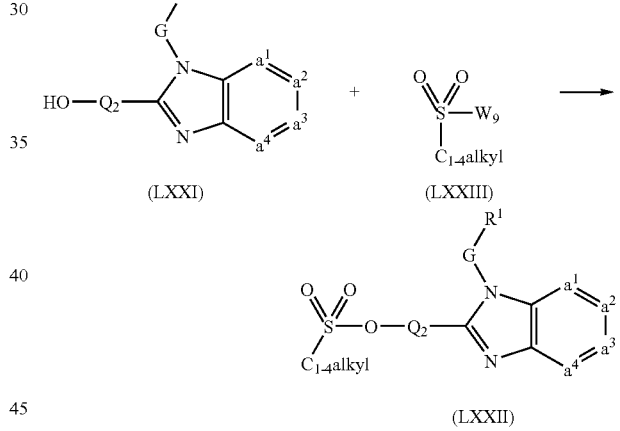

(V)

Intermediates of formula (V) may also be prepared by reacting an intermediate of formula (LXXII) with 1H-isoindole-1,3 (2H)-dione in the presence of a suitable base, such as sodium hydride, and a suitable solvent, such as N,N-dimethylformamide.

Intermediates of formula (V), wherein in the definition of $Q_2$, $R^2$ is $C_{1-10}$alkyl, said $Q_2$ being represented by $C_{1-10}$alkyl-$Q_{1b}$, and said intermediates by formula (V-a), can be prepared by reacting a compound of formula (I-a-3) with an intermediate of formula (LXXIV), wherein $W_{10}$ is a suitable leaving group, such as a halo atom, e.g. chloro, in the presence of a suitable base, such as dipotassium carbonate, and a suitable solvent, such as acetonitrile.

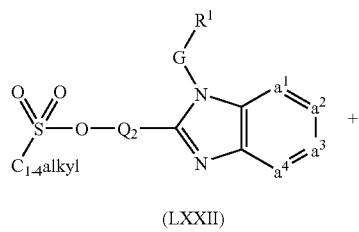

(LXXII)

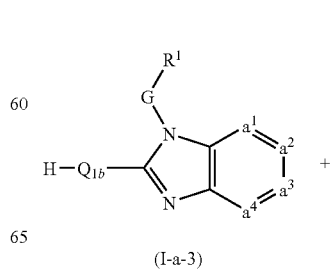

(I-a-3)

-continued

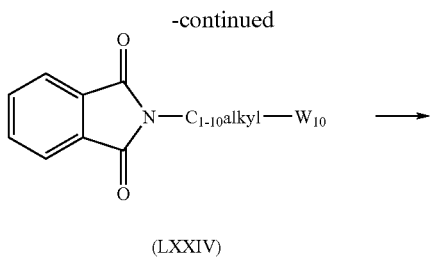

(LXXIV)

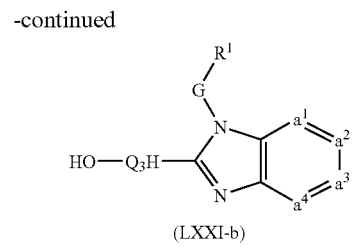

(LXXI-b)

Intermediates of formula (VI) wherein, in the definition of $Q_2$, $R^2$ is $C_{1-10}$alkyl substituted with $N(P)_2$ and the carbon atom adjacent to the nitrogen atom carrying the $R^2$ substituent carries also at least one hydrogen atom, said $Q_2$ being represented by $(P)_2N-C_{1-10}$alkyl-$NH$-$Q_{2a}H$, and said intermediates being represented by formula (VI-a), can be prepared by reductive amination of an intermediate of formula (LXXVI) with an intermediate of formula (LXXVII) in the presence of a suitable reductive agent, such as hydrogen, and a suitable catalyst, such as palladium-on-charcoal, platinum-on-charcoal, and the like, and optionally in the presence of a suitable catalyst poison, such as a thiophene solution. A suitable solvent in this reaction is a reaction-inert solvent, such as an alcohol.

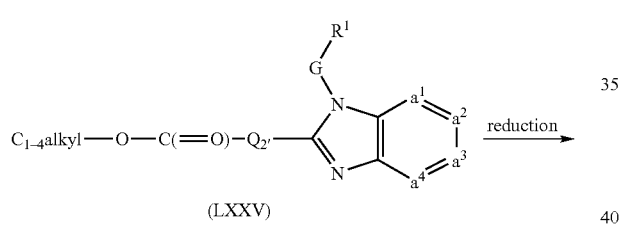

Intermediates of formula (LXXI) wherein, in the definition of $Q_2$, the carbon atom carrying the hydroxy, also carries two hydrogen atoms, said HO-$Q_2$ being represented by HO—$CH_2$-$Q_{2'}$, and said intermediates being represented by formula (LXXI-a), can be prepared by reducing an intermediate of formula (LXXV) in the presence of a suitable reducing agent, such as lithium aluminium hydride, in a suitable reaction-inert solvent, e.g. tetrahydrofuran.

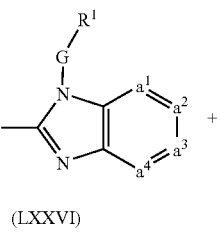

Intermediates of formula (LXXI), wherein, in the definition of $Q_2$, the carbon atom carrying the hydroxy, carries also at least one hydrogen, said HO-$Q_2$ being represented by HO-$Q_3H$, and said intermediates being represented by formula (LXXI-b), can be prepared by reducing an intermediate of formula (IX) with a suitable reducing agent, e.g. sodium borohydride, in a reaction-inert solvent, e.g. an alcohol.

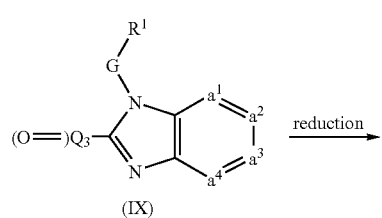

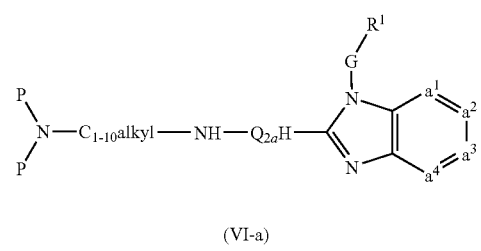

Intermediates of formula (LXXVI) can be prepared by deprotecting an intermediate of formula (LXXVIII) in the presence of a suitable acid, such as hydrochloric acid and the like, in a suitable solvent, e.g. water.

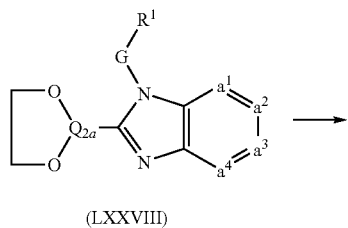

(LXXVIII)

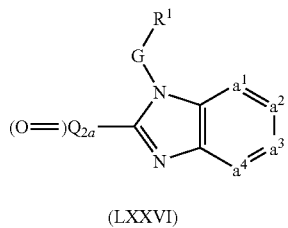

(LXXVI)

Intermediates of formula (IX) may be prepared by deprotecting an intermediate of formula (LXXIX) in the presence of a suitable acid, e.g. hydrochloric acid and the like.

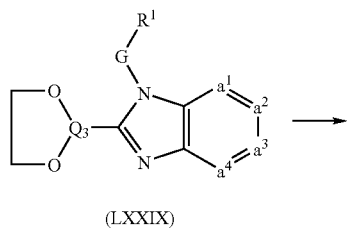

(LXXIX)

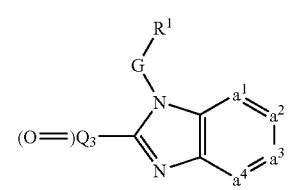

(IX)

Intermediates of formula (LXXIX) can be prepared by reacting an intermediate of formula (LXXX) with an intermediate of formula (III) in the presence of a suitable base, e.g. dipotassium carbonate, in a suitable reaction-inert solvent, e.g. acetonitrile.

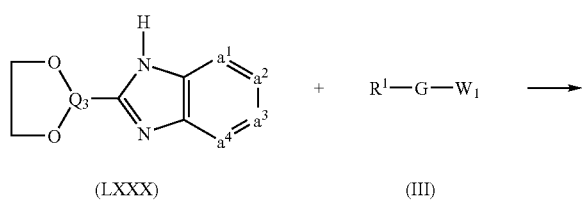

(LXXX)     (III)

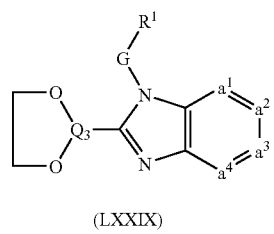

(LXXIX)

Intermediates of formula (LXXX) wherein, in the definition of $Q_3$, the $X^1$ or $X^2$ moiety of the radicals of formula (b-1) to (b-8) represent NH, said $Q_3$ being represented by $Q_{3'}$—NH, and said intermediates being represented by formula (LXXX-a), may be prepared by cyclizing an intermediate of formula (LXXXI) in the presence of mercury oxide and sulphur, in a suitable reaction-inert solvent, e.g. an alcohol.

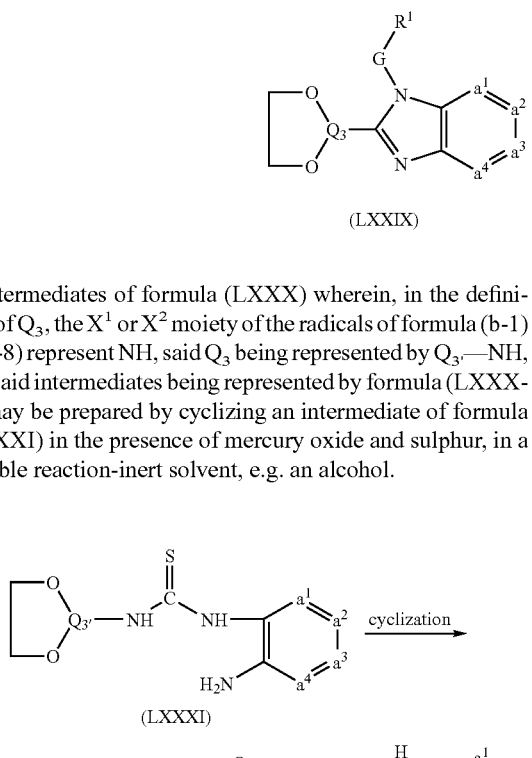

Intermediates of formula (LXXXI) can be prepared by reducing an intermediate of formula (LXXXII) in the presence of a suitable reducing agent, such as hydrogen, in the presence of a suitable catalyst, such as palladium-on-charcoal, platinum-on-charcoal and the like, in a suitable solvent, e.g. a mixture of ammonia in alcohol. Suitable alcohols are methanol, ethanol, 2-propanol and the like.

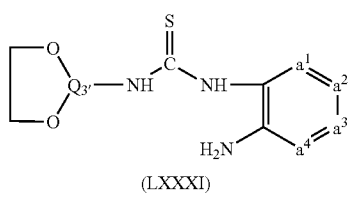

Intermediates of formula (LXXXII) can be prepared by reacting an intermediate of formula (LXXXIII) with an intermediate of formula (LXXXIV) in a suitable reaction-inert solvent, e.g. ethanol.

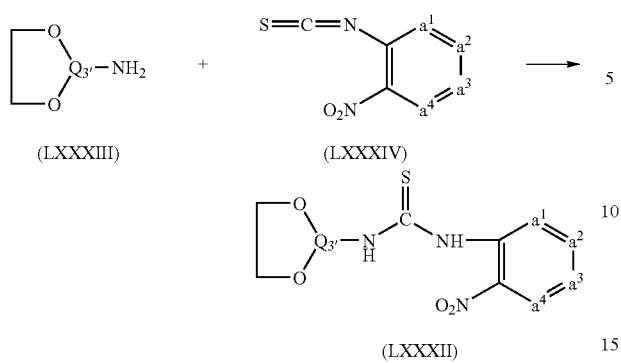

Intermediates of formula (IX), wherein, in the definition of $Q_3$, $R^2$ comprises $C_{1-10}$alkyl, said $Q_3$ being represented by $C_{1-10}$alkyl-$Q_{1b}$, and said intermediates being represented by formula (IX-a), can be prepared by reacting a compound of formula (I-a-3) with a reagent of formula (LXXXV), wherein (O=)$C_{1-10}$alkyl represents a carbonyl derivative of $C_{1-10}$alkyl and wherein $W_{11}$ is a suitable leaving group, such as a halo atom, e.g. bromo, in a reaction-inert solvent, e.g. acetonitrile, in the presence of a suitable base, e.g. dipotassium carbonate.

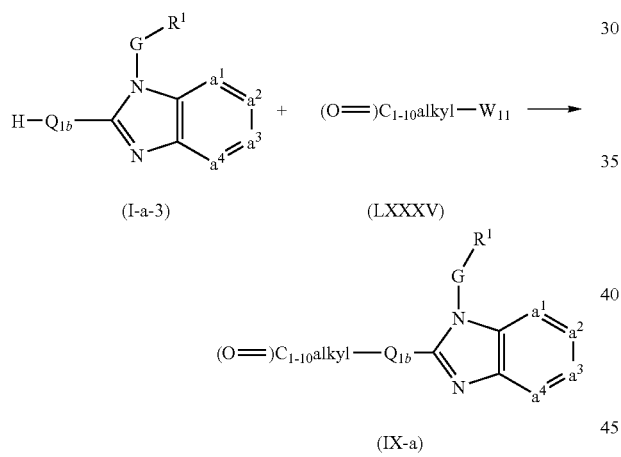

Intermediates of formula (X) wherein $Q_4$ comprises $C_{1-9}$alkyl, said $Q_4$ being represented by $C_{1-9}$alkyl-$Q_{1b}$, and said intermediates being represented by formula (X-a), can be prepared by reacting a compound of formula (I-a-3) with a reagent of formula (LXXXVI) wherein $W_{12}$ represents a suitable leaving group, such as a halo atom, e.g. chloro, in a reaction-inert solvent, e.g. 3-methyl-2-butanone, in the presence of a suitable base, e.g. dipotassium carbonate, sodium bicarbonate and the like.

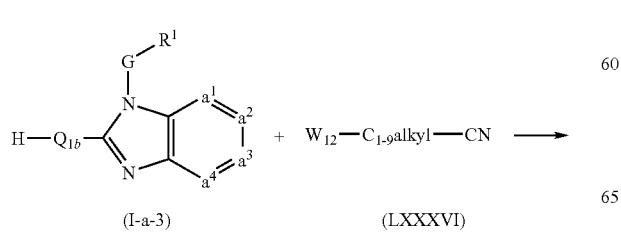

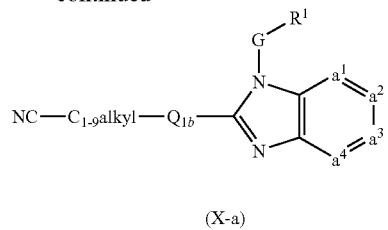

Intermediates of formula (X), wherein NC-$Q_4$ represents NC—($C_{1-9}$alkyl)($R^4$)N—C(=O)-Alk-$X^1$, said intermediates being represented by formula (X-b), can be prepared by reacting an intermediate of formula (LXXXVII) with an intermediate of formula (LXXXVIII) in the presence of di-1H-imidazol-2-yl-methanone, a suitable base, such as N,N-diethyl-ethanamine, and a suitable solvent, such as methylene chloride.

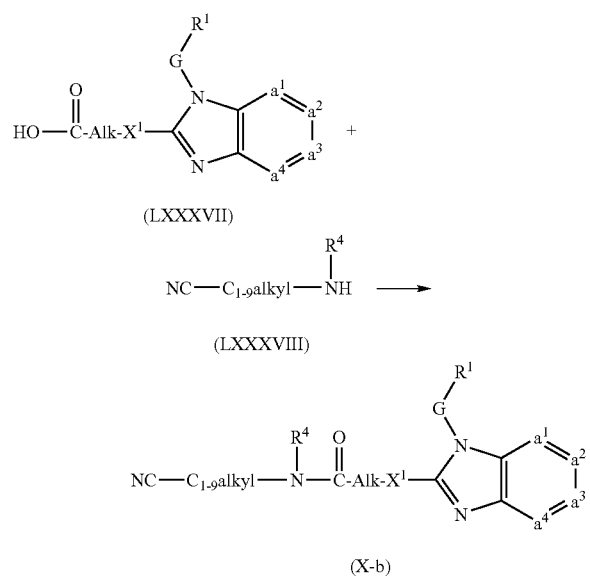

Intermediates of formula (XI), wherein $Q_{4'}$ represents $Q_{1b}$, said intermediates being represented by formula (XI-a), can be prepared by reacting a compound of formula (I-a-3) with an intermediate of formula (LXXXIX), wherein $W_{13}$ represents a suitable leaving group, such as a halo atom, e.g. chloro, in the presence of a suitable base, such as disodium carbonate, and in the presence of a suitable solvent, such as 3-methyl-2-butanone.

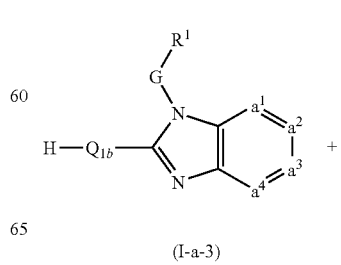

-continued

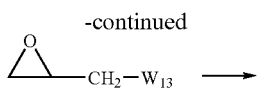

(LXXXIX)

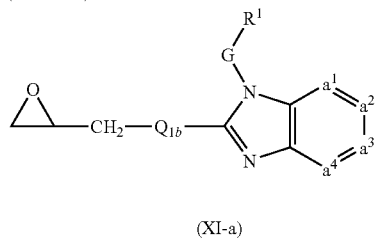

(XI-a)

Intermediates of formula (XIX) can be prepared by reacting an intermediate of formula (XC) with a suitable acid, such as hydrochloric acid.

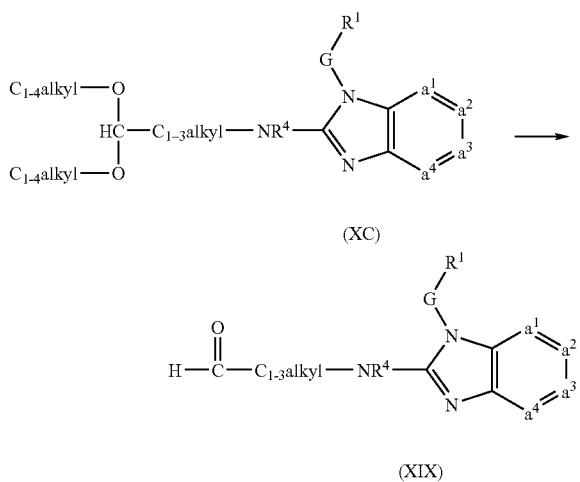

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV).

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The following examples are intended to illustrate the present invention.

A. PREPARATION OF THE INTERMEDIATE COMPOUNDS

EXAMPLE A1 a) $K_2CO_3$ (0.129 mol) was suspended in a solution of ethyl 4-(1H-benzimidazol-2-yl-amino)-1-piperidinecarboxylate (0.0347 mol) and 2-bromo-1-(4-chlorophenyl)ethanone (0.0647 mol) in acetonitrile (150 ml). The mixture was stirred and refluxed for 8 hours, then cooled, poured out into $H_2O$ and extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 97.5/2.5/0.1). The pure fractions were collected and the solvent was evaporated. Part of this fraction (3 g) was taken up in 2-propanone and diethyl ether. The precipitate was filtered off and dried, yielding 2 g of ethyl 4-[[1-[2-(4-chlorophenyl)-2-oxoethyl]-1H-benzimidazol-2-yl]amino]-1-piperidinecarboxylate (interm. 1).

b) A mixture of intermediate (1) (0.015 mol) in HCl 12N (100 ml) was stirred and refluxed for 12 hours, then the solvent was evaporated. Ethylacetate was added. The mixture was basified with a saturated $NaHCO_3$ solution. The precipitate was filtered off, washed with $H_2O$ and with ethylacetate and dried. The residue (5.5 g) was crystallized from ethylacetate. The precipitate was filtered off and dried, yielding 4.8 g of 1-(4-chlorophenyl)-2-[2-(4-piperidinylamino)-1H-benzimidazol-1-yl]ethanone dihydrate (80%) (interm. 2).

EXAMPLE A2 a) NaBH4 (0.034 mol) was added portionwise at 5° C. to a mixture of (±)-1,1-dimethylethyl 4-[[1-(2-oxo-2-phenylethyl)-1H-benzimidazol-2-yl]amino]-1-piperidinecarboxylate (0.034 mol) in tetrahydrofuran (250 ml) and methanol (250 ml). The mixture was stirred at 5° C. and then hydrolyzed cold with $H_2O$. The solvent was evaporated and the residue was taken up in $H_2O$. The precipitate was filtered off, washed with diisopropylether and dried, yielding 11.3 g of (±)-1,1-dimethylethyl 4-[[1-(2-hydroxy-2-phenylethyl)-1H-benzimidazol-2-yl]amino]-1-piperidinecarboxylate (76%) (interm. 3).

b) A mixture of intermediate (3) (0.0183 mol) in tetrahydrofuran (50 ml) was cooled to 0° C. under $N_2$ flow. NaH 80% (0.0366 mol) was added portionwise. The mixture was brought to room temperature, then stirred at room temperature for 30 minutes and cooled again to 0° C. A solution of $CH_3I$ (0.0183 mol) in tetrahydrofuran (50 ml) was added dropwise. The mixture was stirred at room temperature for 2 hours, then cooled, hydrolyzed and extracted with ethylacetate. The organic layer was separated, washed with $H_2O$, dried, filtered and the solvent was evaporated. The residue was purified by column chromatography over silica gel (eluent: $CH_2Cl_2/CH_3OH/NH_4OH$ 98.5/1.5/0.1). The desired fractions were collected and the solvent was evaporated, yielding 5 g of (±)-1,1-dimethylethyl 4-[[1-(2-methoxy-2-phenylethyl)-1H-benzimidazol-2-yl]amino]-1-piperidinecarboxylate (interm. 4).

EXAMPLE A3 a) NaOCH$_3$ (0.2 mol) was added to a mixture of N-(4-piperidinyl)-1H-benzimidazol-2-amine dihydrobromide (0.1 mol) in methanol (389 ml), the mixture was cooled on an ice bath and stirred for 2 hours. Bis(1,1-dimethylethyl)dicarbonate (0.1 mol) was added to a cooled mixture on an ice bath and then stirred for 18 hours at room temperature. The solvent was evaporated and the residue suspended in water/diisopropyl ether. The residue was filtered off, washed with water/diisopropyl ether and dried. The residue was boiled up in CH$_3$OH, yielding 17.46 g of 1,1-dimethylethyl 4-(1H-benzimidazol-2-ylamino)-1-piperidinecarboxylate (55.2%) (interm. 5).

b) A mixture of 3-(benzyloxy)-6-methyl-2-pyridinemethanol (0.0314 mol) and MnO$_2$ (29.52 g) in CH$_2$Cl$_2$ (100 ml) was stirred at room temperature overnight and then purified over silica gel on a glass filter (eluent: CH$_2$Cl$_2$ 100%). The pure fractions were collected and the solvent was evaporated, yielding 6.71 g of 6-methyl-3-(phenylmethoxy)-2-pyridinecarboxaldehyde (94%) (interm. 6).

c) A mixture of intermediate (6) (0.0385 mol) and triethylorthoformiate in the presence of 4-methylbenzenesulfonic acid (0.5 g) in toluene (200 ml) was stirred and refluxed for 6 hours. The solvent was evaporated. The residue was taken up in H$_2$O, Na$_2$CO$_3$ and CH$_2$Cl$_2$. The organic layer was separated, dried, filtered and the solvent was evaporated, yielding 9.6 g of 2-(diethoxymethyl)-6-methyl-3-(phenylmethoxy)pyridine (83%) (interm. 7).

d) Intermediate (7) (0.03185 mol) and intermediate (5) (0.03185 mol) were heated to 150° C. and purified over silica gel on a glass filter (eluent: CH$_2$Cl$_2$/(CH$_3$OH/NH$_3$) 98/2). The pure fractions were collected and the solvent was evaporated, yielding 10.25 g of (±)-1,1-dimethylethyl 4-[[1-[ethoxy[6-methyl-3-(phenylmethoxy)-2-pyridinyl]methyl]-1H-benzimidazol-2-yl]amino]-1-piperidinecarboxylate (56%) (interm. 8).

e) A mixture of 2-(diethoxymethyl)-6-bromo-pyridine (0.03 mol), intermediate 5 (0.03 mol) and 4-methylbenzenesulfonic acid (2 g) in toluene (700 ml) was stirred and refluxed for 20 hours using a water separator. 4-Methylbenzenesulfonic acid was added and the mixture was stirred and refluxed for 48 hours 4-Methylbenzenesulfonic acid was added again and the mixture was stirred and refluxed for another 48 hours. 4-Methylbenzenesulfonic acid was added again. The mixture was stirred and refluxed for 24 hours, then cooled and washed with a diluted NaOH solution. The organic layer was separated, dried, filtered and the solvent was evaporated. The residue was purified by column chromatography over silica gel (eluent: CH$_2$Cl$_2$/C$_2$H$_5$OH 95/5). The pure fractions were collected and the solvent was evaporated. The residue was suspended in petroleum ether. The precipitate was filtered off and dried, yielding 1.4 g of (±)-1,1-dimethylethyl 4-[[1-[(6-bromo-2-pyridinyl]ethoxymethyl]-1H-benzimidazol-2-yl]amino]-1-piperidinecarboxylate (9%) (interm. 33).

EXAMPLE A4 a) A mixture of 2,3-pyridinediamine (0.05 mol) and ethyl 4-(2-ethoxy-2-iminoethyl)-1-piperidinecarboxylate monohydrochloride (0.05 mol) in methanol (150 ml) was stirred and refluxed for 3 days. The solvent was evaporated and the residue was taken up in CH$_2$Cl$_2$. The organic solution was washed with K$_2$CO$_3$ 10%, dried, filtered and the solvent was evaporated. The residue was purified by column chromatography over silica gel (eluent: CH$_2$Cl$_2$/CH$_3$OH/NH$_4$OH 94/6/0.1). The pure fractions were collected and the solvent was evaporated, yielding 7.6 g of ethyl 4-[(1H-imidazo[4,5-b]pyridin-2-yl)methyl]-1-piperidinecarboxylate (52%) (interm. 9).

b) NaH (0.028 mol) was added portionwise at 0° C. to a mixture of intermediate (9) (0.023 mol) in N,N-dimethylformamide (75 ml). 2-Bromo-1-phenylethanone (0.028 mol) was added. The mixture was stirred at room temperature for 1 hour. H$_2$O was added and the mixture was extracted with ethylacetate. The organic layer was separated, dried, filtered and the solvent was evaporated. The residue was purified by column chromatography over silica gel (eluent: CH$_2$Cl$_2$/CH$_3$OH/NH$_4$OH 97.5/2.5/0.1). The pure fractions were collected and the solvent was evaporated, yielding 4.7 g of ethyl 4-[[1-(2-oxo-2-phenylethyl)-1H-imidazo[4,5-b]pyridin-2-yl]methyl]-1-piperidinecarboxylate (50.5%) (interm. 10).

c) NaBH$_4$ (0.0137 mol) was added portionwise at 5° C. under N$_2$ flow to a mixture of intermediate (10) (0.0137 mol) in methanol (100 ml). The mixture was hydrolyzed with H$_2$O and extracted with ethylacetate. The organic layer was separated, dried, filtered and the solvent was evaporated, yielding 5.6 g of (±)-ethyl 4-[[1-(2-hydroxy-2-phenylethyl)-1H-imidazo[4,5-b]pyridin-2-yl]methyl]-1-piperidinecarboxylate (interm. 11).

EXAMPLE A5

A mixture of (±)-1-[ethoxy(6-methyl-2-pyridinyl)methyl]-N-(4-piperidinyl)-1H-benzimidazol-2-amine (0.00205 mol), 1-chloro-2-propanone (0.00308 mol) and K$_2$CO$_3$ (0.0041 mol) in acetonitrile (8 ml) was stirred and refluxed for 8 hours. H$_2$O was added and the mixture was extracted with ethylacetate. The organic layer was separated, dried, filtered and the solvent was evaporated. The residue was purified by column chromatography over silica gel (eluent: CH$_2$Cl$_2$/CH$_3$OH/NH$_4$OH 97/3/0.1). The pure fractions were collected and the solvent was evaporated, yielding: 0.67 g of (±)-1-[4-[[1-[ethoxy(6-methyl-2-pyridinyl)methyl]-1H-benzimidazol-2-yl]amino]-1-piperidinyl]-2-propanone (77%) (interm. 12).

EXAMPLE A6

4-Methylbenzenesulfonyl chloride (0.2222 mol) was added portionwise at 10° C. to a mixture of 1,1-dimethylethyl [1-(hydroxymethyl)-2-methylpropyl]carbamoate (0.202 mol) in pyridine (65 ml). The mixture was stirred at 10° C. for 2 hours. H$_2$O (75 ml) was added at 10° C. The precipitate was filtered off, washed with H$_2$O and taken up in CH$_2$Cl$_2$. The organic solution was washed with H$_2$O, dried, filtered and the solvent was evaporated, yielding 49 g of (±)-1,1-dimethylethyl [1-[[[(4-methylphenyl)-sulfonyl]oxy]methyl]-2-methylpropyl]carbamate (68%) (interm. 13).

EXAMPLE A7 a) A mixture of (±)-1,1-dimethylethyl 4-[[1-[[6-bromo-2-pyridinyl]ethoxymethyl]-1H-benzimidazol-2-yl]amino]-1-piperidinecarboxylate (0.00189 mol) (interm. 33), Pd (0.026 g), (R)-(+)-2,2'-bis(diphenyl-phosphino)-1,1'-binaphtyl (0.046 g) and NH(CH$_3$)$_2$ gas (10 g) in tetrahydrofuran (200 ml) was stirred in an autoclave at 100° C. for 16 hours under pressure of CO (30 atm). The mixture was filtered and the filtrate was evaporated. The residue was purified over silica gel on a glass filter (eluent: CH$_2$Cl$_2$/(CH$_3$OH/NH$_3$) 99/1). The pure fractions were collected and the solvents was evaporated, yielding 0.8 g of (±)-1,1-dimethylethyl 4-[[1-[[6-(dimethylamino)-2-pyridinyl]ethoxymethyl]-1H-benzimidazol-2-yl]amino]-1-piperidinecarboxylate (86%) (interm. 14).

b) A mixture of intermediate 33 (0.0032 mol), Pd(OAc)$_2$ (0.030 g) and 1,3-propanediylbis[diphenylphosphine] (0.110 g) in tetrahydrofuran (100 ml) under ammonia (liq., 10 atm) and CO (gas, 30 atm) was stirred for 16 hours at 100° C. The solvent was evaporated. The residue was purified over silica gel on a glass filter (eluent: CH$_2$Cl$_2$/(CH$_3$OH/NH$_3$) 98/2). The pure fractions were collected and the solvent was evaporated, yielding 0.15 g of interm. 41.

EXAMPLE A8

A mixture of α-[[(3-amino-2-pyridinyl)amino]methyl]benzenemethanol (0.043 mol) and ethyl 4-isothiocyanato-1-piperidinecarboxylate (0.047 mol) in toluene (200 ml) was stirred and refluxed for 30 minutes. N,N'-methanetetraylbiscyclohexanamine (0.065 mol) was added and the mixture was stirred and refluxed overnight. The solvent was evaporated. The residue was purified by column chromatography over silica gel (eluent: CH$_2$Cl$_2$/CH$_3$OH$_4$OH 96/4/0.2). The pure fractions were collected and the solvent was evaporated. Part of the residue (1.5 g) was crystallized from diisopropyl ether. The precipitate was filtered off and dried, yielding 1.35 g of (±)-ethyl 4-[[1-(2-hydroxy-2-phenylethyl)-1H-imidazo[4,5-b]pyridin-2-yl]amino]-1-piperidinecarboxylate (interm. 15).

EXAMPLE A9

Reaction under N$_2$ flow. NaH 60% (0.02 mol) was added to a mixture of 1.1-dimethylethyl 4-(1H-benzimidazol-2-ylamino)-1-piperidinecarboxylate (0.02 mol) in N,N-di-methylformamide (100 ml). The mixture was stirred at 40° C. for 1 hour. 6-(Epoxyethyl)-2-picoline (0.02 mol) in a small amount of N,N-dimethylformamide was added. The mixture was stirred at 100° C. overnight. The solvent was evaporated. The residue was taken up in H$_2$O and CH$_2$Cl$_2$. The organic layer was separated, dried, filtered and the solvent was evaporated. The residue was purified by column chromatography over silica gel (eluent: CH$_2$Cl$_2$/CH$_3$OH 95/5 and 90/10). The pure fractions were collected and the solvent was evaporated, yielding 3.5 g of (±)-1,1-dimethylethyl 4-[[1-[2-hydroxy-2-(6-methyl-2-pyridinyl)ethyl]-1H-benzimidazol-2-yl]amino]-1-piperidinecarboxylate (interm. 16).

Tables 1, 2 and 3 list intermediates which were prepared analogous to one of the above examples.

TABLE 1

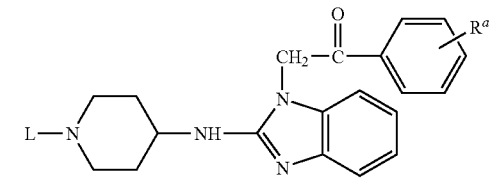

| Int. No. | Ex. No. | L | R$^a$ | Physical data |
|---|---|---|---|---|
| 17 | A1b | H | 2-Cl | |
| 18 | A1b | H | 4-OCH$_3$ | |
| 19 | A1b | H | 3-Cl | H$_2$O (1:1) |
| 20 | A1b | H | 3-F | H$_2$O (1.2) |
| 2 | A1b | H | 4-Cl | H$_2$O (1:2) |
| 21 | A1b | H | 3-CH$_3$ | |
| 22 | A1b | H | 2-CH$_3$ | H$_2$O (1:1) |
| 23 | A1a | —C(=O)—O—C$_2$H$_5$ | 4-CH$_3$ | |
| 24 | A1b | H | 4-CH$_3$ | H$_2$O (1:1); mp. 180° C. |
| 25 | A1b | H | 3-OCH$_3$ | H$_2$O (1:1), HCl (1:1); mp. 220° C. |
| 26 | A1b | H | 2-F | |

TABLE 2

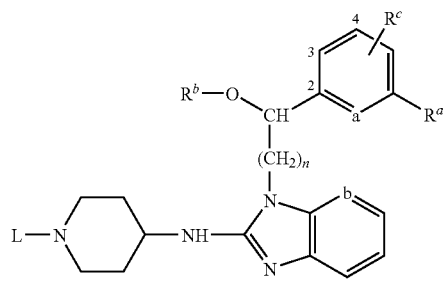

| Int. No. | Ex. No. | L | n | a | b | $R^a$ | $R^b$ | $R^c$ | Physical data; mp. |
|---|---|---|---|---|---|---|---|---|---|
| 27 | A3e | —C(=O)—O—C(CH$_3$)$_3$ | 0 | N | CH | CH$_3$ | —C$_2$H$_5$ | H | |
| 28 | A3d | —C(=O)—O—C(CH$_3$)$_3$ | 0 | N | CH | CH$_3$ | phenyl-CH$_2$—O—(CH$_2$)$_3$— | H | |
| 29 | A3d | —C(=O)—O—C(CH$_3$)$_3$ | 0 | N | CH | CH$_3$ | —(CH$_2$)$_2$—O—C$_2$H$_5$ | H | |
| 30 | A3d | —C(=O)—O—C(CH$_3$)$_3$ | 0 | N | CH | CH$_3$ | —[(CH$_2$)$_2$—O]$_2$—CH$_3$ | H | |
| 31 | A3d | —C(=O)—O—C(CH$_3$)$_3$ | 0 | N | CH | Phenyl | —(CH$_2$)$_2$—O—C$_2$H$_5$ | H | |
| 32 | A3d | —C(=O)—O—C(CH$_3$)$_3$ | 0 | N | CH | —CH$_2$—O—CH$_3$ | —CH$_3$ | H | |
| 33 | A3e | —C(=O)—O—C(CH$_3$)$_3$ | 0 | N | CH | Br | —C$_2$H$_5$ | H | |
| 34 | A3d | —CH$_2$-phenyl | 0 | N | CH | H | —C$_2$H$_5$ | H | |
| 35 | A5 | —CH$_2$—C(=O)—CH(CH$_3$)$_2$ | 0 | N | CH | CH$_3$ | —C$_2$H$_5$ | H | |
| 36 | A5 | —CH$_2$—C(=O)—CH(CH$_3$)$_2$ | 0 | N | CH | CH$_3$ | —(CH$_2$)$_2$—O—C$_2$H$_5$ | H | |
| 37 | A5 | —CH$_2$—C(=O)—CH(CH$_3$)$_2$ | 0 | N | CH | CH$_3$ | —[(CH$_2$)$_2$—O]$_2$—CH$_3$ | H | |
| 38 | A5 | —CH$_2$—C(=O)—CH(CH$_3$)$_2$ | 0 | N | CH | Phenyl | —(CH$_2$)$_2$—O—C$_2$H$_5$ | H | |
| 40 | A3d | —C(=O)—O—C(CH$_3$)$_3$ | 0 | N | CH | CH$_3$ | —C$_2$H$_5$ | 3-O-benzyl | |
| 41 | A7b | —C(=O)—O—C(CH$_3$)$_3$ | 0 | N | CH | —CO—NH$_2$ | —C$_2$H$_5$ | H | |
| 42 | A7b | —C(=O)—O—C(CH$_3$)$_3$ | 0 | N | CH | —CO—N(CH$_3$)$_2$ | —C$_2$H$_5$ | H | |
| 16 | A9 | —C(=O)—O—C(CH$_3$)$_3$ | 1 | N | CH | CH$_3$ | H | H | |
| 44 | A3d | —C(=O)—O—C(CH$_3$)$_3$ | 0 | N | CH | CH$_3$ | —(CH$_2$)$_2$—OCH$_3$ | H | |
| 4 | A2b | —C(=O)—O—C(CH$_3$)$_3$ | 1 | CH | CH | H | CH$_3$ | H | |
| 15 | A8 | —C(=O)—O—C$_2$H$_5$ | 1 | CH | N | H | H | H | 85° C. |
| 47 | A7a | —C(=O)—O—C(CH$_3$)$_3$ | 0 | N | CH | —N(CH$_3$)$_2$ | C$_2$H$_5$ | H | |

TABLE 3

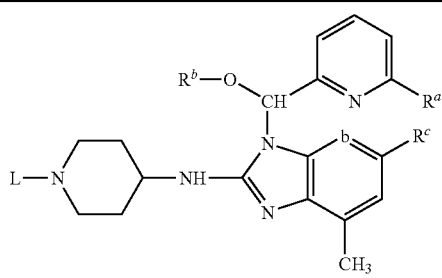

| Int. No. | Ex. No. | b | $R^a$ | $R^b$ | $R^c$ | L | Physical data; mp. |
|---|---|---|---|---|---|---|---|
| 48 | A3d | CH | Br | —CH$_2$—CH$_3$ | H | —C(=O)—O—C(CH$_3$)$_3$ | |
| 49 | A5 | CH | CH$_3$ | —C$_2$H$_4$—O—CH$_3$ | Cl | —CH$_2$—C(=O)—CH(CH$_3$)$_2$ | |
| 50 | A3d | CH | CH$_3$ | —C$_2$H$_4$—O—CH$_3$ | Cl | —C(=O)—O—C(CH$_3$)$_3$ | |
| 51 | A5 | N | CH$_3$ | —C$_2$H$_4$—O—CH$_3$ | H | —CH$_2$—C(=O)—CH(CH$_3$)$_2$ | |
| 52 | A3d | N | CH$_3$ | —C$_2$H$_4$—O—CH$_3$ | H | —CH$_2$—C$_6$H$_5$ | |

B. PREPARATION OF THE FINAL COMPOUNDS

EXAMPLE B1

A mixture of intermediate (4) (0.0102 mol) in HCl 3N (80 ml) and 2-propanol (10 ml) was stirred at 40° C. for 2 hours. The mixture was brought to room temperature and poured out on ice. $CH_2Cl_2$ was added. The mixture was basified with $K_2CO_3$ solid, stirred at room temperature for 1 hour and extracted with $CH_2Cl_2$. The organic layer was separated, washed with $H_2O$, dried, filtered and the solvent was evaporated. The residue was crystallized from diethyl ether and $CH_3OH$. The precipitate was filtered off and dried, yielding 2.9 g of (±)-1-(2-methoxy-2-phenylethyl)-N-(4-piperidinyl)-1H-benzimidazol-2-amine (81%) (compound 1).

EXAMPLE B2

A mixture of intermediate (11) (0.0139 mol) and KOH (0.1 mol) in 2-propanol (200 ml) was stirred and refluxed overnight. The solvent was evaporated and the residue was purified by column chromatography over silica gel (eluent: $CH_2Cl_2/CH_3OH/NH_4OH$ 80/20/3). The pure fractions were collected and the solvent was evaporated. The residue was converted into the ethanedioic acid salt (1:2) with ethanedioic acid. The mixture was crystallized from 2-propanone. The precipitate was filtered off and dried, yielding 3.9 g of (±)-α-phenyl-2-(4-piperidinylmethyl)-1H-imidazo[4,5-b]pyridine-1-ethanol ethanedioate (1:2) (compound 2).

EXAMPLE B3 a) A mixture of intermediate (8) (0.00175 mol) in trifluoroacetic acid (20 ml) and $CH_2Cl_2$ (50 ml) was stirred at room temperature for 2 hours, poured out into ice water and alkalized with a NaOH solution. $CH_2Cl_2$ was added. The organic layer was separated, dried, filtered and the solvent was evaporated. The residue was purified over silica gel on a glass filter (eluent: $CH_2Cl_2/(CH_3OH/NH_3)$ 90/10). The pure fractions were collected and the solvent was evaporated. The residue was converted into the hydrochloric acid salt (1:3). The precipitate was filtered off and dried, yielding 0.48 g of (±)-1-[ethoxy[6-methyl-(3-phenylmethoxy)-2-pyridinyl]methyl]-N-(4-piperidinyl)-1H-benzimidazol-2-amine trihydrochloride dihydrate 2-propanolate (1:1) (compound 3).

b) A mixture of (±)-1,1-dimethylethyl 4-[[1-[(6-bromo-2-pyridinyl)ethoxymethyl]-1H-benzimidazol-2-yl]amino]-1-piperidinecarboxylate (0.0026 mol) in 2-propanol (30 ml) and $HBr/CH_3COOH$ (2 ml) was stirred and refluxed for 2 hours and then cooled. The solvent was evaporated. The residue was taken up in $H_2O$ and $CH_2Cl_2$. The mixture was alkalized with a NaOH solution. The organic layer was separated, washed with $H_2O$, dried, filtered and the solvent evaporated. The residue was purified by column chromatography over silica gel (eluent: $CH_2Cl_2/NH_3$ 90/10). The pure fractions were collected and the solvent was evaporated. The residue was suspended in petroleum ether. The precipitate was filtered off and dried. This fraction was recrystallized from a small amount of $CH_3CN$. The precipitate was filtered off and dried, yielding 0.22 g of (±)-1-[(6-bromo-2-pyridinyl)ethoxymethyl]-N-(4-piperidinyl)-1H-benzimidazol-2-amine (19.6%) (compound 4).

EXAMPLE B4

A mixture of (±)-1-[ethoxy(2-pyridinyl)methyl]-N-[1-(phenylmethyl)-4-piperidinyl]-1H-benzimidazol-2-amine (0.011 mol) in methanol (150 ml) was hydrogenated for 4 days with Pd/C 10% (2 g) as a catalyst. After uptake of $H_2$ (1 equivalent), the catalyst was filtered off and the filtrate was evaporated. The residue was purified by column chromatography over silica gel (eluent: $CH_2Cl_2/(CH_3OH/NH_3)$ 90/10). The pure fractions were collected and the solvent was evaporated, yielding 1.5 g of (±)-1-[ethoxy-(2-pyridinyl)methyl]-N-(4-piperidinyl)-2-benzimidazol-2-amine (39%) (compound 5).

EXAMPLE B5

$NaBH_4$ (0.0078 mol) was added portionwise to a mixture of intermediate (2) (0.0078 mol) in tetrahydrofuran (50 ml) and methanol (50 ml), and the mixture was stirred at 5° C. under $N_2$ flow for 2 hours. The mixture was hydrolyzed cold with $H_2O$ (3 ml) and the solvent was evaporated. The precipitate was filtered off, washed with $H_2O$ and dried.

The residue (3 g) was crystallized from diisopropyl ether. The precipitate was filtered off and dried, yielding 2.9 g of (±)-α-(4-chlorophenyl)-2-(4-piperidinylamino)-1H-benzimidazole-1-ethanol (100%) (compound 6).

EXAMPLE B6

A mixture of compound (4) (0.0035 mol), 1,1-dimethylethyl (2-bromomethyl)carbamoate (0.005 mol) and $Na_2CO_3$ (0.01 mol) in 2-butanone (100 ml) was stirred and refluxed for 20 hours. $H_2O$ was added. The organic layer was separated, dried, filtered and the solvent was evaporated. The residue was purified by column chromatography over silica gel (eluent: $CH_2Cl_2/CH_3OH$ 95/5 to 90/10). The pure fractions were collected and the solvent was evaporated, yielding 1.3 g of (±)-1,1-dimethylethyl [2-[4-[[1-[(6-bromo-2-pyridinyl)ethoxymethyl]-1H-benzimidazol-2-yl]amino]-1-piperidinyl]-ethyl]carbamate (compound 7).

EXAMPLE B7

A mixture of compound (4) (0.00348 mol), intermediate (13) (0.00348 mol) and $K_2CO_3$ (0.01392 mol) in acetonitrile (20 ml) and N,N-dimethylformamide (4 ml) was stirred at 60° C. for 4 hours (1 equivalent of intermediate (13) was added every hour) and then cooled. The solvent was evaporated. The residue was taken up in $CH_2Cl_2$. The organic solution was washed with $H_2O$, dried, filtered and the solvent was evaporated. The residue was purified by column chromatography over silica gel (eluent: $CH_2Cl_2/CH_3OH/NH_4OH$ 96.5/3.5/0.1). Two pure fractions were collected and their solvents were evaporated, yielding Ig of (±)-1,1-dimethylethyl [1-[[4-[[1-[(6-bromo-2-pyridinyl)ethoxymethyl]-1H-benzimidazol-2-yl]amino]-1-piperidinyl]methyl]-2-methylpropyl]carbamate (47%) (compound 8).

EXAMPLE B8

A mixture of compound (7) (0.0026 mol) in 2-propanol (30 ml) and HBr/acetic acid (2 ml) was stirred and refluxed for 90 minutes and then cooled. The solvent was evaporated. The residue was taken up in $CH_2Cl_2$ and $H_2O$. The organic layer was separated, dried, filtered and the solvent was evaporated. The residue was purified by column chromatography over silica gel (eluent: $CH_2Cl_2/(CH_3OH/NH_3)$ 90/10). The pure fractions were collected and the solvent was evaporated. The residue was suspended in diisopropyl ether. The precipitate was filtered off and dried. This fraction was purified again by column chromatography over silica gel (eluent: $CH_2Cl_2/$ (CH₃OH/NH₃) 90/10). The pure fractions were collected and the solvent was evaporated. The residue was suspended in diisopropyl ether. The precipitate was filtered off and dried, yielding 0.23 g of (±)-N-[1-(2-aminoethyl)-4-piperidinyl]-1-[(6-bromo-2-pyridinyl)ethoxymethyl]-1H-benzimidazol-2-amine (compound 9).

EXAMPLE B9

A mixture of compound (8) (0.00162 mol) in 2-propanol/HCl (1 ml) and 2-propanol (10 ml) was stirred and refluxed for 1 hour and then cooled. The solvent was evaporated. The residue was taken up in CH₂Cl₂. The organic solution was washed with K₂CO₃ 10% and with H₂O, dried, filtered and the solvent was evaporated. The residue was purified by column chromatography (eluent: CH₂Cl₂/CH₃OH/NH₄OH 94/6/1). The pure fractions were collected and the solvent was evaporated, yielding 0.23 g of (±)-N-[1-(2-amino-3-methylbutyl)-4-piperidinyl]-1-[(6-bromo-2-pyridinyl)-ethoxymethyl]-1H-benzimidazol-2-amine (27%) (compound 10).

EXAMPLE B10

A mixture of (±)-1,1-dimethylethyl [2-[4-[[1-[ethoxy[6-methyl-3-(phenylmethoxy)-2-pyridinyl]methyl]-1H-benzimidazol-2-yl]amino]-1-piperidinyl]ethyl]carbamate (0.0016 mol) and KOH (1 g) in sec-butanol (25 ml) was stirred and refluxed for 6 hours. The solvent was evaporated. The residue was purified over silica gel on a glass filter (eluent: CH₂Cl₂/(CH₃OH/NH₃) 95/5, 93/7 to 90/10). The pure fractions were collected and the solvent was evaporated. The residue was converted into the hydrochloric acid salt (1:3). The precipitate was filtered off and dried, yielding 0.5 g of (±)-N-[1-(2-aminoethyl)-4-piperidinyl]-1-[ethoxy[6-methyl-3-(phenylmethoxy)-2-pyridinyl]-methyl]-1H-benzimidazol-2-amine trihydrochloride dihydrate (compound 11).

EXAMPLE B11

A mixture of intermediate (12) (0.0016 mol) and benzenemethanamine (0.0048 mol) in methanol (7 ml) was hydrogenated at 40° C. under a 5 bar pressure for 8 hours with Pd/C (0.07 g) as a catalyst. After uptake of H₂ (1 equivalent), the catalyst was filtered through celite, washed with CH₃OH and CH₂Cl₂ and the filtrate was evaporated. The residue was purified by column chromatography over silica gel (eluent: CH₂Cl₂/CH₃OH/NH₄OH 93/7/0.7). The pure fractions were collected and the solvent was evaporated. The residue was crystallized from diethyl ether. The precipitate was filtered off and dried, yielding 0.4 g of (±)-N-[1-(2-aminopropyl)-4-piperidinyl]-1-[ethoxy(6-methyl-2-pyridinyl)methyl]-1H-benzimidazol-2-amine (59%) (compound 12).

EXAMPLE B12

A mixture of (±)-N-[1-(2-aminoethyl)-4-piperidinyl]-1-[(6-methyl-2-pyridinyl) [2-(phenylmethoxy)ethoxy]methyl]-1H-benzimidazol-2-amine (0.003 mol) in methanol (150 ml) was stirred at room temperature with Pd/C 10% (0.5 g) as a catalyst. After uptake of H₂ (1 equivalent), the catalyst was filtered off and the filtrate was evaporated. The residue was purified by column chromatography over silica gel (eluent: CH₂Cl₂/(CH₃OH/NH₃) 90/10). The pure fractions were collected and the solvent was evaporated. The residue was suspended in petroleum ether. The precipitate was filtered off and dried, yielding 0.23 g of (±)-2-[[2-[[1-(2-aminoethyl)-4-piperidinyl]-amino]-1H-benzimidazol-2-yl](6-methyl-2-pyridinyl)methoxy]ethanol monohydrate (18%) (compound 13).

EXAMPLE B13

A mixture of (±)-1-[4-[[1-(2-ethoxyethoxy)(6-methyl-2-pyridinyl)methyl]-1H-benzimidazol-2-yl]amino]-1-piperidinyl]-3-methyl-2-butanone (0.0032 mol) in NH₃/CH₃OH (200 ml) was hydrogenated for 3 days at 20° C. with Rh/Al₂O₃ 5% (1 g) as a catalyst in the presence of a thiophene solution (2 ml). After uptake of H₂ (1 equivalent), the catalyst was filtered off and the filtrate was evaporated. The residue was purified by column chromatography over silica gel (eluent: CH₂Cl₂/(CH₃OH/NH₃) 95/5). The pure fractions were collected and the solvent was evaporated. The residue was crystallized from diisopropyl ether, filtered off and dried, yielding 0.58 g of (±)-N-[1-(2-amino-3-methylbutyl)-4-piperidinyl]-1-[(2-ethoxyethoxy)(6-methyl-2-pyridinyl)methyl]-1H-benzimidazol-2-amine (compound 14).

Tables 4 to 8 list the compounds of formula (I) which were prepared according to one of the above examples.

TABLE 4

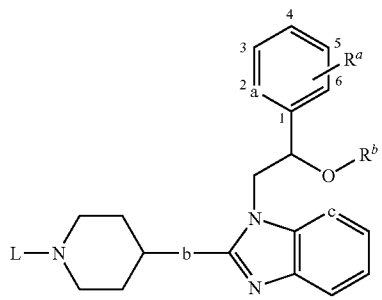

| Comp. No. | Ex. No. | b | c | a | L | R^b | R^a | Physical data |
|---|---|---|---|---|---|---|---|---|
| 1 | B1 | NH | CH | CH | H | CH₃ | H | mp. 146° C. |
| 2 | B2 | CH₂ | N | CH | H | H | H | mp. 150° C.; ethanedioate (1:2) |
| 6 | B5 | NH | CH | CH | H | H | 4-Cl | |
| 31 | B2 | NH | N | CH | H | H | H | mp. 210° C. |
| 32 | B5 | NH | CH | CH | H | H | 2-Cl | |

TABLE 4-continued

| Comp. No. | Ex. No. | b | c | a | L | $R^b$ | $R^a$ | Physical data |
|---|---|---|---|---|---|---|---|---|
| 33 | B5 | NH | CH | CH | H | H | 4-OCH$_3$ | |
| 34 | B5 | NH | CH | CH | H | H | 3-Cl | |
| 35 | B5 | NH | CH | CH | H | H | 2-CH$_3$ | |
| 36 | B5 | NH | CH | CH | H | H | 3-CH$_3$ | mp. 145° C. |
| 37 | B5 | NH | CH | CH | H | H | 3-OCH$_3$ | mp. 162° C. |
| 38 | B5 | NH | CH | CH | H | H | 3-F | mp. >230° C. |
| 39 | B5 | NH | CH | CH | H | H | 2-F | mp. 205° C. |
| 40 | B5 | NH | CH | CH | H | H | 4-CH$_3$ | mp. 207° C. |
| 47 | B6 | NH | CH | N | * | H | 3-CH$_3$ | |

* = —(CH$_2$)$_2$—NH—C(=O)—O—C(CH$_3$)$_3$

TABLE 5

| Comp. No. | Ex. No. | L | $R^a$ | $R^b$ | $R^c$ | Physical data |
|---|---|---|---|---|---|---|
| 3 | B3a | H | CH$_3$ | —C$_2$H$_5$ | ** | HCl (1:3); H$_2$O (1:2); 2-propanolate (1:1) |
| 4 | B3b | H | Br | —C$_2$H$_5$ | H | |
| 5 | B4 | H | H | —C$_2$H$_5$ | H | |
| 9 | B8 | —(CH$_2$)$_2$—NH$_2$ | Br | —C$_2$H$_5$ | H | |
| 11 | B10 | —(CH$_2$)$_2$—NH$_2$ | CH$_3$ | —C$_2$H$_5$ | ** | HCl (1:3); H$_2$O (1:2) |
| 13 | B12 | —(CH$_2$)$_2$—NH$_2$ | CH$_3$ | —C$_2$H$_4$—OH | H | H$_2$O (1:1) |
| 15 | B1 | H | CH$_3$ | —C$_2$H$_5$ | H | |
| 16 | B1 | H | CH$_3$ | —(CH$_2$)$_2$—O—C$_2$H$_5$ | H | |
| 17 | B1 | H | CH$_3$ | —[(CH$_2$)$_2$—O]$_2$—CH$_3$ | H | |
| 18 | B1 | H | CH$_3$ | —C$_2$H$_5$ | H | (A) |
| 19 | B1 | H | Br | —C$_2$H$_5$ | H | (A) |
| 20 | B1 | H | Br | —C$_2$H$_5$ | H | (B) |
| 21 | B1 | H | CH$_3$ | —C$_2$H$_5$ | H | (B) |
| 22 | B1 | H | —CH$_2$—O—CH$_3$ | —CH$_3$ | H | |
| 23 | B1 | H | Phenyl | —(CH$_2$)$_2$—O—C$_2$H$_5$ | H | |
| 24 | B1 | H | —N(CH$_3$)$_2$ | —C$_2$H$_5$ | H | |
| 25 | B1 | H | —C(=O)—NH$_2$ | —C$_2$H$_5$ | H | |
| 26 | B1 | H | —C(=O)—N(CH$_3$)$_2$ | —C$_2$H$_5$ | H | |
| 27 | B1 | H | CH$_3$ | H | H | |
| 28 | B1 | H | CH$_3$ | H | H | HCl (1:3); H$_2$O (1:1) |
| 29 | B1 | H | CH$_3$ | —(CH$_2$)$_2$—O—CH$_2$—phenyl | H | |
| 30 | B1 | H | CH$_3$ | —(CH$_2$)$_2$—O—CH$_3$ | H | HCl (1:1) |
| 63 | B9 | —(CH$_2$)$_2$—NH$_2$ | CH$_3$ | —C$_2$H$_5$ | H | |
| 64 | B9 | —(CH$_2$)$_2$—NH$_2$ | CH$_3$ | —C$_2$H$_4$—O—C$_2$H$_5$ | H | |
| 65 | B9 | —(CH$_2$)$_2$—NH$_2$ | H | —C$_2$H$_5$ | H | HCl (1:4); H$_2$O (1:1) |
| 66 | B9 | —(CH$_2$)$_2$—NH$_2$ | H | —[(CH$_2$)$_2$—O]$_2$—CH$_3$ | H | |
| 78 | B9 | —(CH$_2$)$_2$—NH$_2$ | phenyl | —C$_2$H$_4$—O—C$_2$H$_5$ | H | HCl (1:3); H$_2$O (1:1) |
| 79 | B9 | —(CH$_2$)$_2$—NH$_2$ | —N(CH$_3$)$_2$ | —C$_2$H$_5$ | H | HCl (1:4); H$_2$O (1:3) |
| 80 | B9 | —(CH$_2$)$_2$—NH$_2$ | CH$_3$ | H | H | HCl (1:4); H$_2$O (1;1) |

TABLE 5-continued

| Comp. No. | Ex. No. | L | $R^a$ | $R^b$ | $R^c$ | Physical data |
|---|---|---|---|---|---|---|
| 81 | B9 | —(CH$_2$)$_2$—NH$_2$ | CH$_3$ | —C$_2$H$_4$—O—CH$_2$—phenyl | H | |
| 82 | B9 | —(CH$_2$)$_2$—NH$_2$ | CH$_3$ | —C$_2$H$_4$—O—CH$_3$ | H | |

\*\* = —O—CH$_2$-phenyl
(A) indicates the first isolated stereoisomeric form
(B) indicates the second isolated stereoisomeric form

TABLE 6

| Comp. No. | Ex. No. | $R^a$ | $R^b$ | $R^c$ | $R^d$ | Physical data |
|---|---|---|---|---|---|---|
| 7 | B6 | Br | —C$_2$H$_5$ | H | H | |
| 8 | B7 | Br | —C$_2$H$_5$ | H | —CH(CH$_3$)$_2$ | |
| 41 | B6 | CH$_3$ | —C$_2$H$_5$ | H | H | |
| 42 | B6 | CH$_3$ | —C$_2$H$_4$—O—C$_2$H$_5$ | H | H | |
| 43 | B6 | H | —C$_2$H$_5$ | H | H | |
| 44 | B6 | CH$_3$ | —[C$_2$H$_4$—O]$_2$—CH$_3$ | H | H | |
| 45 | B6 | phenyl | —C$_2$H$_4$—O—C$_2$H$_5$ | H | H | |
| 46 | B6 | —N(CH$_3$)$_2$ | —C$_2$H$_5$ | H | H | |
| 48 | B6 | CH$_3$ | —C$_2$H$_4$—O—CH$_2$-phenyl | H | H | |
| 49 | B6 | CH$_3$ | —C$_2$H$_4$—O—CH$_3$ | H | H | |
| 50 | B6 | CH$_3$ | —C$_2$H$_5$ | —O—CH$_2$-phenyl | H | |
| 51 | B7 | CH$_3$ | —C$_2$H$_5$ | H | —CH(CH$_3$)$_2$ | [(A),(S)] |
| 52 | B7 | CH$_3$ | —C$_2$H$_5$ | H | —CH(CH$_3$)$_2$ | [(A),(R)] |
| 53 | B7 | Br | —C$_2$H$_5$ | H | —CH(CH$_3$)$_2$ | [(A),(S)] |
| 54 | B7 | Br | —C$_2$H$_5$ | H | —CH(CH$_3$)$_2$ | [(A),(R)] |
| 55 | B7 | Br | —C$_2$H$_5$ | H | —CH(CH$_3$)$_2$ | [(B),(R)] |
| 56 | B7 | Br | —C$_2$H$_5$ | H | —CH(CH$_3$)$_2$ | [(B),(S)] |
| 57 | B7 | CH$_3$ | —C$_2$H$_5$ | H | —CH(CH$_3$)$_2$ | [(B),(S)] |
| 59 | B7 | CH$_3$ | —C$_2$H$_5$ | H | —CH$_3$ | [(A),(R)] |
| 60 | B7 | CH$_3$ | —C$_2$H$_5$ | H | —CH$_3$ | [(A),(S)] |
| 61 | B7 | CH$_3$ | —C$_2$H$_5$ | H | —CH$_3$ | [(B),(S)] |
| 62 | B7 | CH$_3$ | —C$_2$H$_5$ | H | —CH$_3$ | [(B),(R)] |

(A) indicates the first isolated stereoisomeric form
(B) indicates the second isolated stereoisomeric form

TABLE 7

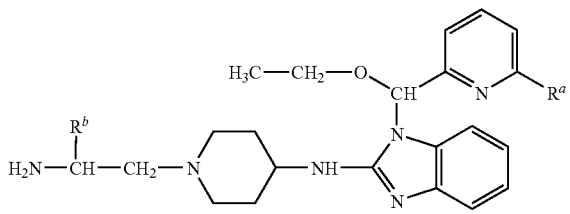

| Comp. No. | Ex. No. | $R^a$ | $R^b$ | Physical Data |
|---|---|---|---|---|
| 10 | B9 | Br | —CH(CH$_3$)$_2$ | mp. 184° C. |
| 12 | B11 | CH$_3$ | —CH$_3$ | mp. 114° C. |
| 58 | B7 | CH$_3$ | —CH(CH$_3$)$_2$ | [(B),(R)]; H$_2$O (1:1); mp. 60° C.; [α]$_{20}^D$ (5.20 mg/1 ml in methanol) = −131.15 |
| 67 | B9 | CH$_3$ | —CH(CH$_3$)$_2$ | [(A),(S)]; H$_2$O (1:1); mp. 91° C.; [α]$_{20}^D$ (4.50 mg/1 ml in methanol) = +126.44 |
| 68 | B9 | CH$_3$ | —CH(CH$_3$)$_2$ | [(A),(R)]; H$_2$O (1:1); mp. 60° C.; [α]$_{20}^D$ (5.42 mg/1 ml in methanol) = +62.18 |
| 69 | B9 | Br | —CH(CH$_3$)$_2$ | [(A),(S)]; mp. 70° C.; [α]$_{20}^D$ (4.78 mg/1 ml in methanol) = +133.26 |
| 70 | B9 | Br | —CH(CH$_3$)$_2$ | [(A),(R)]; mp. 60° C.; [α]$_{20}^D$ (5.43 mg/1 ml in methanol) = +66.85 |
| 71 | B9 | Br | —CH(CH$_3$)$_2$ | [(B),(R)]; H$_2$O (1:1); mp. 60° C.; [α]$_{20}^D$ (5.08 mg/1 ml in methanol) = −136.02 |
| 72 | B9 | Br | —CH(CH$_3$)$_2$ | [(B),(S)]; [α]$_{20}^D$ (5.00 mg/1 ml in methanol) = −58.00 |
| 73 | B9 | CH$_3$ | —CH(CH$_3$)$_2$ | [(B),(S)]; H$_2$O (1:1); mp. 60° C.; [α]$_{20}^D$ (4.37 mg/1 ml in methanol) = −60.18 |
| 74 | B9 | CH$_3$ | —CH$_3$ | [(A),(R)]; H$_2$O (1:1); mp. 70° C.; [α]$_{20}^D$ (5.00 mg/1 ml in methanol) = +73.00 |
| 75 | B9 | CH$_3$ | —CH$_3$ | [(A),(S)]; H$_2$O (1:1); mp. <50° C.; [α]$_{20}^D$ (4.60 mg/1 ml in methanol) = +126.52 |
| 76 | B9 | CH$_3$ | —CH$_3$ | [(B),(S)]; H$_2$O (1:1); mp. <50° C.; [α$_{20}^D$ (4.69 mg/1 ml in methanol) = −57.78 |
| 77 | B9 | CH$_3$ | —CH$_3$ | [(B),(R)]; H$_2$O (1:2); mp. <50° C.; [α]$_{20}^D$ (4.74 mg/1 ml in methanol) = −127.64 |
| 83 | B11 | CH$_3$ | —CH(CH$_3$)$_2$ | mp. 110° C. |

(A) indicates the first isolated stereoisomeric form
(B) indicates the second isolated stereoisomeric form

TABLE 8

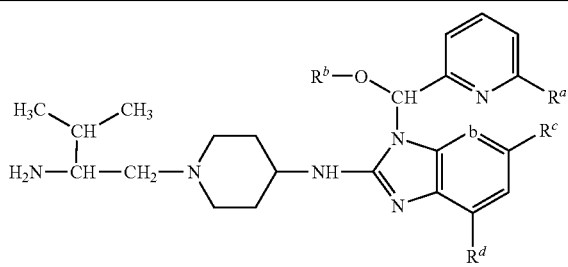

| Comp. No. | Ex. No. | b | $R^a$ | $R^b$ | $R^c$ | $R^d$ | Physical Data |
|---|---|---|---|---|---|---|---|
| 14 | B13 | CH | CH$_3$ | —C$_2$H$_4$—O—C$_2$H$_5$ | H | H | |
| 84 | B13 | CH | CH$_3$ | —[(CH$_2$)$_2$—O]$_2$—CH$_3$ | H | H | |
| 85 | B13 | CH | phenyl | —C$_2$H$_4$—O—C$_2$H$_5$ | H | H | |
| 86 | B13 | CH | CH$_3$ | —C$_2$H$_4$—O—CH$_3$ | H | H | |
| 87 | B7 | CH | Br | CH$_2$—CH$_3$ | H | CH$_3$ | H$_2$O; mp. 60° C. |
| 88 | B13 | CH | CH$_3$ | —C$_2$H$_4$—O—CH$_3$ | Cl | CH$_3$ | HCl (1:3)/H$_2$O (1:3) |
| 89 | B13 | N | CH$_3$ | —C$_2$H$_4$—O—CH$_3$ | H | CH$_3$ | |

C. PHARMACOLOGICAL EXAMPLE

EXAMPLE C1

In Vitro Screening for Activity Against Respiratory Syncytial Virus

The percent protection against cytopathology caused by viruses (antiviral activity or $IC_{50}$) achieved by tested compounds and their cytotoxicity ($CC_{50}$) were both calculated from dose-response curves. The selectivity of the antiviral effect is represented by the selectivity index (SI), calculated by dividing the $CC_{50}$ (cytotoxic dose for 50% of the cells) by the $IC_{50}$ (antiviral activity for 50% of the cells).

Automated tetrazolium-based colorimetric assays were used for determination of $IC_{50}$ and $CC_{50}$ of test compounds. Flat-bottom, 96-well plastic microtiter trays were filled with 180 μl of Eagle's Basal Medium, supplemented with 5% FCS (0% for FLU) and mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension (4×10⁵ cells/ml) of HeLa cells was added to all wells in a volume of 50 μl. The cultures were incubated at 37° C. in a 5% $CO_2$ atmosphere. Seven days after infection the cytotoxicity and the antiviral activity was examined spectrophotometrically. To each well of the microtiter tray, 25 μl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

Particular $IC_{50}$, $CC_{50}$ and SI values are listed in Table 9 hereinbelow.

TABLE 9

| Co. No. | $IC_{50}$ (μM) | $CC_{50}$ (μM) | SI |
|---|---|---|---|
| 87 | 0.00032 | 10.12 | 31623 |
| 10 | 0.0006 | 37.86 | 63096 |
| 88 | 0.002 | 20 | 10000 |
| 67 | 0.004 | 63.40 | 15849 |
| 13 | 0.0126 | >100.08 | >7943 |
| 58 | 0.0501 | 79.41 | 1585 |
| 11 | 0.1259 | 9.95 | 79 |
| 80 | 1.2589 | >99.45 | >79 |

The invention claimed is:

1. A compound of formula

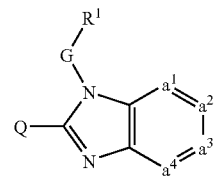

(I)

an addition salt or stereochemically isomeric form thereof wherein

-$a^1$=$a^2$-$a^3$=$a^4$- represents a bivalent radical of formula

—CH=CH—CH=N—  (a-5);

wherein each hydrogen atom in the (a-5) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, mono- or di($C_{1-4}$alkyl)amino$C_{1-6}$alkyl, $C_{1-6}$alkyloxycarbonyl, hydroxy$C_{1-6}$alkyl, or a radical of formula

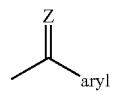

wherein -Z is O, CH—C(=O)—$NR^{5a}R^{5b}$, $CH_2$, CH—$C_{1-6}$ alkyl, N—OH or N—O—$C_{1-6}$alkyl;

Q is a radical of formula

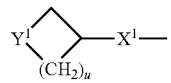

(b-4)

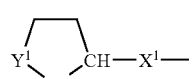

(b-5)

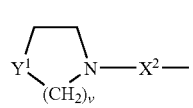

(b-6)

wherein $Y^1$ is a bivalent radical of formula —$NR^2$— or —CH($NR^2R^4$)—;

$X^1$ is $NR^4$, S, S(=O), S(=O)$_2$, O, $CH_2$, C(=O), C(=$CH_2$), CH(OH), CH($CH_3$), CH($OCH_3$), CH($SCH_3$), CH($NR^{5a}R^{5b}$), $CH_2$—$NR^4$ or $NR^4$—$CH_2$;

$X^2$ is a direct bond, $CH_2$, C(=O), $NR^4$, $C_{1-4}$alkyl-$NR^4$, $NR^4$—$C_{1-4}$alkyl;

u is 2 or 3;

v is 2; and whereby each hydrogen atom in the carbocycles and the heterocycles defined in radicals (b-4), (b-5), and (b-6) may optionally be replaced by $R^3$; with the proviso that when $R^3$ is hydroxy or $C_{1-6}$alkyloxy, then $R^3$ can not replace a hydrogen atom in the α position relative to a nitrogen atom;

G is $C_{1-10}$alkanediyl substituted with one or more hydroxy, $C_{1-6}$alkyloxy, aryl$C_{1-6}$alkyloxy, $C_{1-6}$alkylthio, aryl$C_{1-6}$ alkylthio, HO(—CH$_2$—CH$_2$—O)$_n$—, C$_{1-6}$alkyloxy(—CH$_2$—CH$_2$—O)$_n$— or arylC$_{1-6}$alkyloxy(—CH$_2$—CH$_2$—O)$_n$—;

R$^1$ is a monocyclic heterocycle or aryl; said heterocycle being selected from piperidinyl, piperazinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl; and each heterocycle may optionally be substituted with 1 or where possible more substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl—SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$;

each n independently is 1, 2, 3 or 4;

R$^2$ is hydrogen, formyl, C$_{1-6}$alkylcarbonyl, Hetcarbonyl, pyrrolidinyl, piperidinyl, homopiperidinyl, C$_{3-7}$cycloalkyl substituted with N(R$^6$)$_2$, or C$_{1-10}$alkyl substituted with N(R$^6$)$_2$ and optionally with a second, third or fourth substituent selected from amino, hydroxy, C$_{3-7}$cycloalkyl, C$_{2-5}$alkanediyl, piperidinyl, mono- or di(C$_{1-6}$alkyl)amino, C$_{1-6}$alkyloxycarbonylamino, aryl and aryloxy;

R$^3$ is hydrogen, hydroxy, C$_{1-6}$alkyl, C$_{1-6}$alkyloxy, arylC$_{1-6}$alkyl or arylC$_{1-6}$alkyloxy;

R$^4$ is hydrogen, C$_{1-6}$alkyl or arylC$_{1-6}$alkyl;

R$^{5a}$, R$^{5b}$, R$^{5c}$ and R$^{5d}$ each independently are hydrogen or C$_{1-6}$alkyl; or R$^{5a}$ and R$^{5b}$, or R$^{5c}$ and R$^{5d}$ taken together form a bivalent radical of formula —(CH$_2$)$_s$— wherein s is 4 or 5;

R$^6$ is hydrogen, C$_{1-4}$alkyl, formyl, hydroxyC$_{1-6}$alkyl, C$_{1-6}$alkylcarbonyl or C$_{1-6}$alkyloxycarbonyl;

aryl is phenyl or phenyl substituted with 1 or more substituents selected from halo, hydroxy, C$_{1-6}$alkyl, hydroxyC$_{1-6}$alkyl, polyhaloC$_{1-6}$alkyl, and C$_{1-6}$alkyloxy; and Het is pyridyl, pyrimidinyl, pyrazinyl, or pyridazinyl.

2. A compound according to claim 1, wherein R$^1$ is phenyl optionally substituted with halo, C$_{1-6}$alkyl or C$_{1-4}$alkyloxy; or pyridyl optionally substituted with 1 or more substituents selected from arylC$_{1-6}$alkyloxy, C$_{1-6}$alkyloxyC$_{1-6}$alkyl, aryl, mono- or di(C$_{1-6}$alkyl)amino, C(=O)—NR$^{5c}$R$^{5d}$, halo or C$_{1-6}$alkyl.

3. A compound according to claim 1, wherein G is C$_{1-4}$alkanediyl substituted with hydroxy, C$_{1-6}$alkyloxy, HO(—CH$_2$—CH$_2$—O)$_n$—, C$_{1-6}$alkyloxy(—CH$_2$—CH$_2$—O)$_n$— or arylC$_{1-6}$alkyloxy(—CH$_2$—CH$_2$—O)$_n$—.

4. A compound according to claim 1, wherein Q is a radical of formula (b-5) wherein v is 2 and Y$^1$ is —NR$^2$—.

5. A compound according to claim 1, wherein X$^1$ is NH or CH$_2$.

6. A compound according to claim 1, wherein R$^2$ is hydrogen or C$_{1-10}$alkyl substituted with NHR$^6$ wherein R$^6$ is hydrogen or C$_{1-6}$alkyloxycarbonyl.

7. A method of treating a respiratory syncytial viral infection, comprising the step of administering a therapeutically effective amount of a compound of claim 1.

8. A pharmaceutical composition, comprising a pharmaceutically acceptable carrier, and as active ingredient a therapeutically effective amount of a compound of claim 1.

9. A process of preparing a composition as claimed in claim 8, comprising the step of intimately mixing said carrier with said compound.

10. A process of preparing a compound as claimed in claim 1, comprising at least one step selected from the group consisting of:

a) reacting an intermediate of formula (II-a) or (II-b) with an intermediate of formula (III)

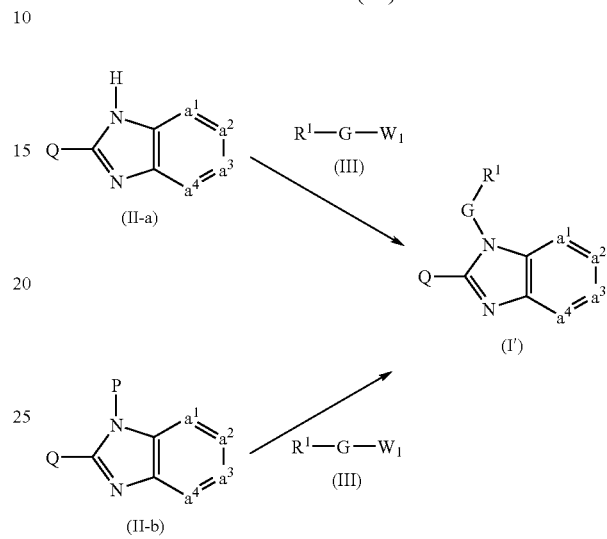

with R$^1$, G, Q and -a$^1$=a$^2$-a$^3$=a$^4$- defined as in claim 1, and W$_1$ being a leaving group, in the presence of a base and in a reaction-inert solvent;

b) deprotecting an intermediate of formula (IV)

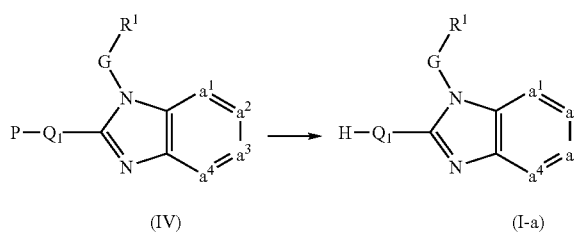

with R$^1$, G, and -a$^1$=a$^2$-a$^3$=a$^4$- defined as in claim 1, H-Q$_1$ being defined as Q according to claim 1 provided that R$^2$ or at least one R$^6$ substituent is hydrogen, and P being a protective group;

c) deprotecting and reducing an intermediate of formula (IV-a)

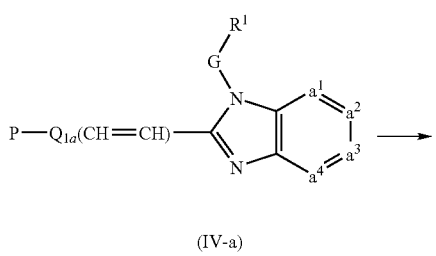

-continued

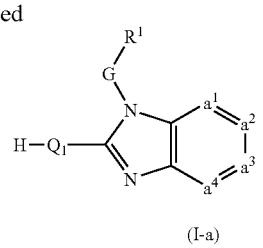

(I-a)

with $R^1$, G, and -$a^1$=$a^2$-$a^3$=$a^4$- defined as in claim 1, H-$Q_1$ being defined as Q according to claim 1 provided that $R^2$ or at least one $R^6$ substituent is hydrogen, $Q_{1a}$ (CH=CH) being defined as $Q_1$ provided that $Q_1$ comprises an unsaturated bond, and P being a protective group;

d) deprotecting an intermediate of formula (V)

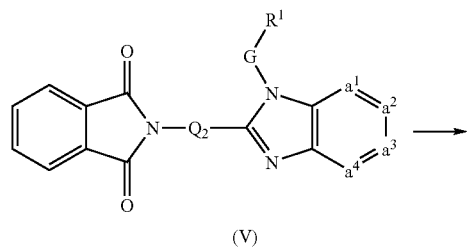

(V)

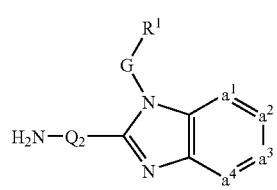

(I-a-1)

with $R^1$, G, and -$a^1$=$a^2$-$a^3$=$a^4$- defined as in claim 1, and $H_2N$-$Q_2$ being defined as Q according to claim 1 provided that both $R^6$ substituents are hydrogen or $R^2$ and $R^4$ are both hydrogen;

e) deprotecting an intermediate of formula (VI)

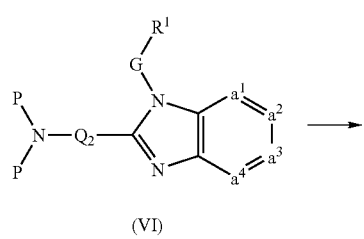

(VI)

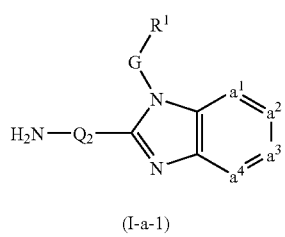

(I-a-1)

with $R^1$, G, and -$a^1$=$a^2$-$a^3$=$a^4$- defined as in claim 1, and $H_2N$-$Q_2$ being defined as Q according to claim 1 provided that both $R^6$ substituents are hydrogen or $R^2$ and $R^4$ are both hydrogen, and P being a protective group;

f) deprotecting an intermediate of formula (VII) or (VIII)

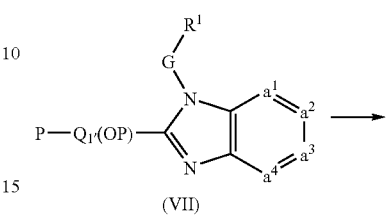

(VII)

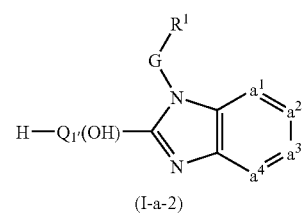

(I-a-2)

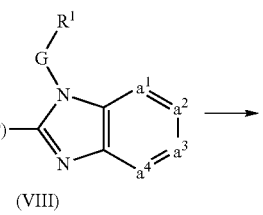

(VIII)

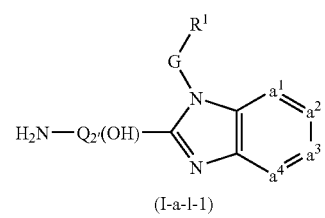

(I-a-1-1)

with $R^1$, G, and -$a^1$=$a^2$-$a^3$=$a^4$- defined as in claim 1, H-$Q_{1'}$(OH) being defined as Q according to claim 1 provided that $R^2$ or at least one $R^6$ substituent is hydrogen and provided that Q comprises a hydroxy moiety, $H_2N$-$Q_{2'}$(OH) being defined as Q according to claim 1 provided that both $R^6$ substituents are hydrogen or $R^2$ and $R^4$ are both hydrogen and provided that Q comprises a hydroxy moiety, and P being a protective group;

g) amination of an intermediate of formula (IX)

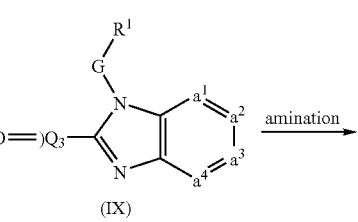

(IX)

-continued

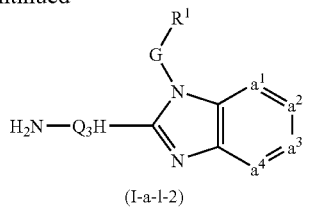

(I-a-1-2)

with $R^1$, G, and -$a^1$=$a^2$-$a^3$=$a^4$- defined as in claim 1, and $H_2N$-$Q_3H$ being defined as Q according to claim 1 provided that both $R^6$ substituents are hydrogen or $R^2$ and $R^4$ are both hydrogen, and the carbon adjacent to the nitrogen carrying the $R^6$, or $R^2$ and $R^4$ substituents contains at least one hydrogen, in the presence of an amination reagent;

h) reducing an intermediate of formula (X)

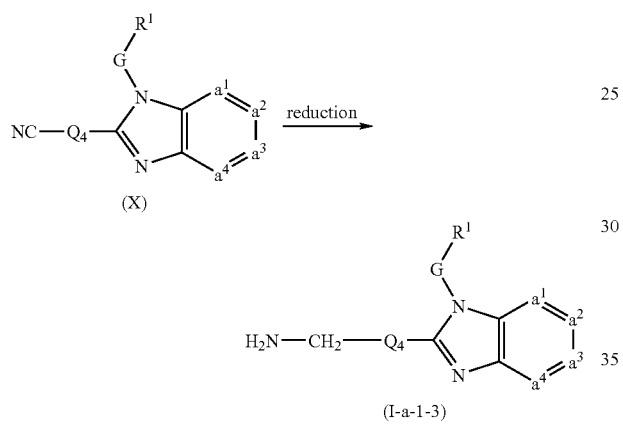

with $R^1$, G, and -$a^1$=$a^2$-$a^3$=$a^4$- defined as in claim 1, and $H_2N$—$CH_2$-$Q_4$ being defined as Q according to claim 1 provided that Q comprises a —$CH_2$—$NH_2$ moiety, in the presence of a reducing agent;

i) reducing an intermediate of formula (X-a)

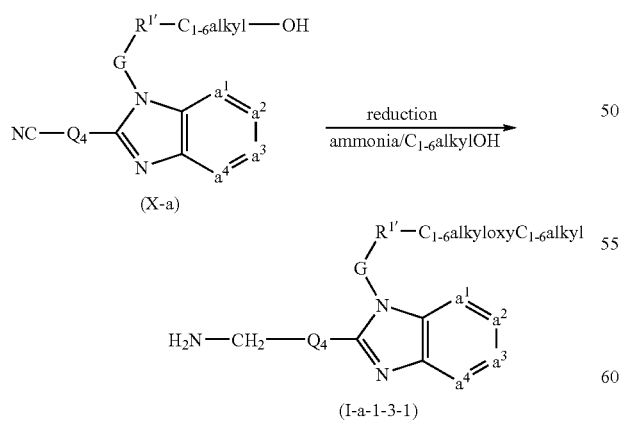

with G, and -$a^1$=$a^2$-$a^3$=$a^4$- defined as in claim 1, $H_2N$—$CH_2$-$Q_4$ being defined as Q according to claim 1 provided that Q comprises a —$CH_2$—$NH_2$ moiety, and $R^{1'}$ being defined as $R^1$ according to claim 1 provided that it comprises at least one substituent, in the presence of a reducing agent and solvent;

j) amination of an intermediate of formula (XI)

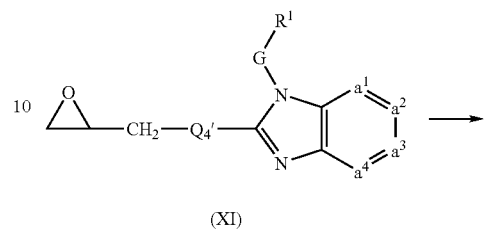

(XI)

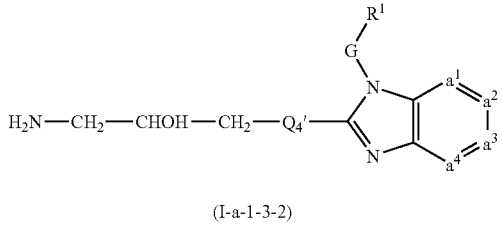

(I-a-1-3-2)

with $R^1$, G, and -$a^1$=$a^2$-$a^3$=$a^4$- defined as in claim 1, and $H_2N$—$CH_2$—CHOH—$CH_2$-$Q_4'$ being defined as Q according to claim 1 provided that Q comprises a $CH_2$—CHOH—$CH_2$—$NH_2$ moiety, in the presence of an amination reagent;

k) reacting an intermediate of formula (XII) with formic acid, formamide and ammonia

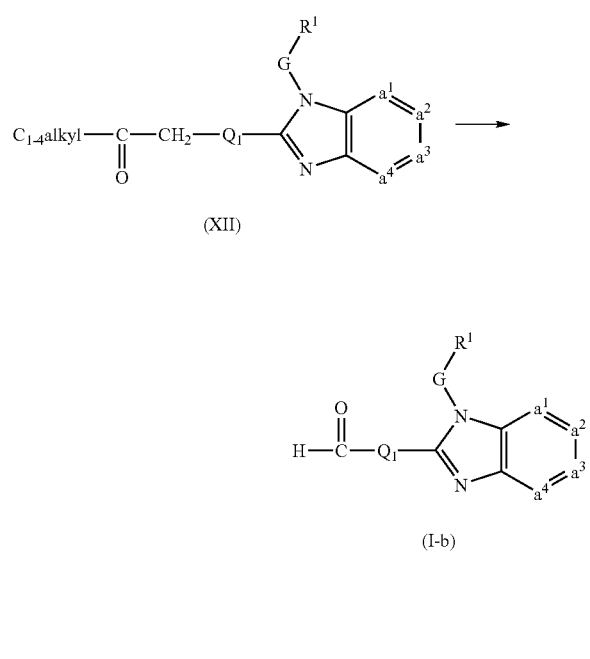

with $R^1$, G, and -$a^1$=$a^2$-$a^{3=a4}$- defined as in claim 1, and H—C(=O)-$Q_1$ being defined as Q according to claim 1 provided that $R^2$ or at least one $R^6$ substituent is formyl;

l) amination of an intermediate of formula (XIII) by reaction with an intermediate of formula (XIV)

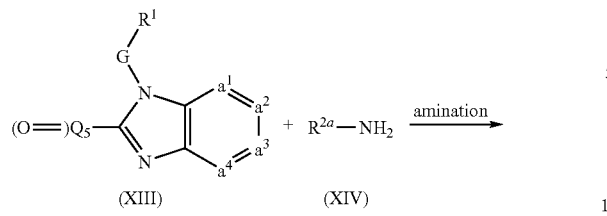

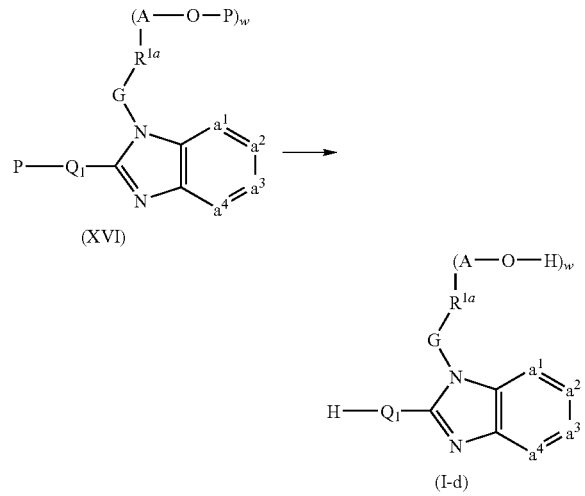

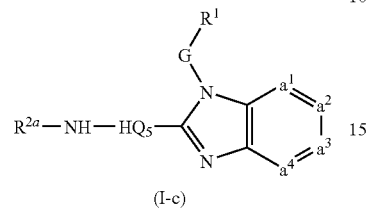

with $R^1$, G, and $-a^1=a^2-a^3=a^4-$ defined as in claim 1, and $R^{2a}$—NH—HQ$_5$ being defined as Q according to claim 1 provided that $R^2$ is other than hydrogen and is represented by $R^{2a}$, $R^4$ is hydrogen, and the carbon atom adjacent to the nitrogen atom carrying the $R^2$ and $R^4$ substituents, carries also at least one hydrogen atom, in the presence of a reducing agent;

m) reducing an intermediate of formula (XV)

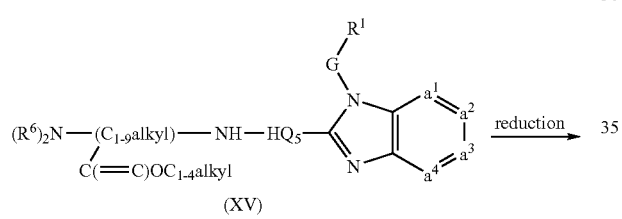

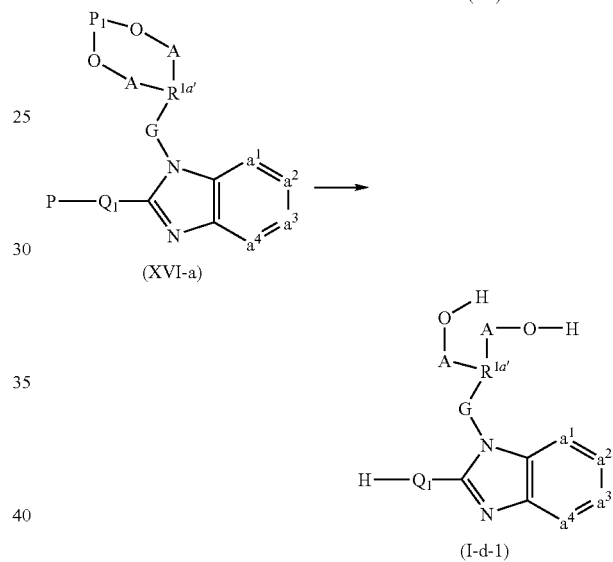

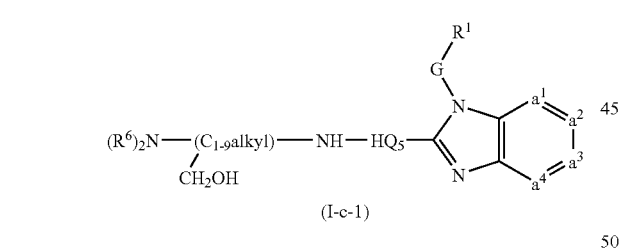

with $R^1$, G, and $-a^1=a^2-a^3=a^4-$ defined as in claim 1, and $(R^6)_2$N—[$(C_{1-9}$alkyl)CH$_2$OH]—NH—HQ$_5$ being defined as Q according to claim 1 provided that $R^2$ is other than hydrogen and is represented by $C_{1-10}$alkyl substituted with $N(R_6)_2$ and with hydroxy, and the carbon atom carrying the hydroxy, carries also two hydrogen atoms, and provided that $R^4$ is hydrogen, and the carbon atom adjacent to the nitrogen atom carrying the $R^2$ and $R^4$ substituents, carries also at least one hydrogen atom, with a reducing agent;

n) deprotecting an intermediate of formula (XVI), (XVI-a) or (XVI-b)

with G, and $-a^1=a^2-a^3=a^4-$ defined as in claim 1, and H-Q$_1$ being defined as Q according to claim 1 provided that $R^2$ or at least one $R^6$ substituent is hydrogen, and $R^{1a}$-(A-O-H)$_w$, $R^{1a'}$-(A-O-H)$_2$ and $R^{1a''}$-(A-O-H)$_3$ being defined as $R^1$ according to claim 1 provided that $R^1$ is substituted with hydroxy, hydroxyC$_{1-6}$alkyl, or HO(-CH$_2$-CH$_2$-O)$_n$-, with w being an integer from 1 to 4 and P or P$_1$ being a protecting group, with an acid;

o) amination of an intermediate of formula (XVII)

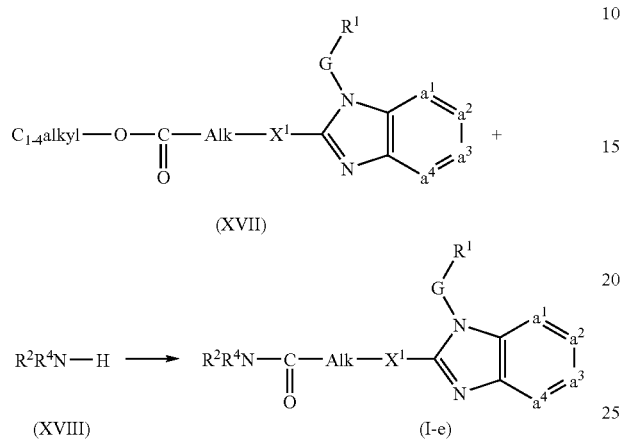

(XVII)

(XVIII)        (I-e)

with $R^1$, G, -a$^1$=a$^2$-a$^3$=a$^4$-, Alk, X$^1$ R$^2$ and R$^4$ defined as in claim 1, in the presence of an amination agent;

p) amination of an intermediate of formula (XIX)

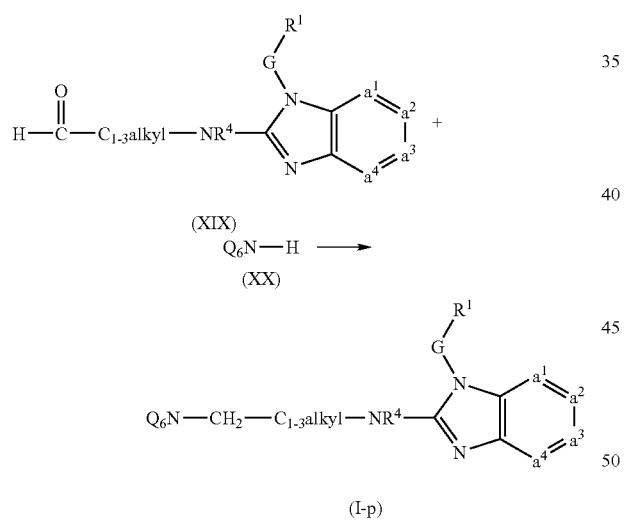

(XIX)

Q$_6$N-H ⟶
(XX)

(I-p)

with $R^1$, G, and -a$^1$=a$^2$-a$^3$=a$^4$- defined as in claim 1, and Q$_6$N-CH$_2$-C$_{1-3}$alkyl-NR$^4$ being defined as Q according to claim 1 provided that in the definition of Q, X$^2$ is C$_{2-4}$alkyl-NR$^4$, in the presence of an amination agent;

q) deprotecting an intermediate of formula (XXI)

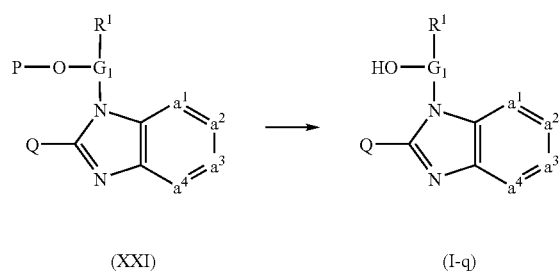

(XXI)        (I-q)

with $R^1$, Q, and -a$^1$=a$^2$-a$^3$=a$^4$- defined as in claim 1, and HO-G$_1$ being defined as G according to claim 1 provided that G is substituted with hydroxy or HO-(CH$_2$CH$_2$O-)$_n$; and r) reducing an intermediate of formula (XXII)

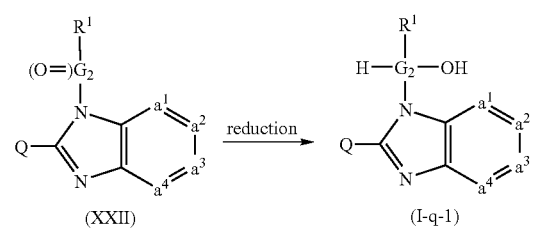

(XXII)        (I-q-1)

with $R^1$, Q, and -a$^1$=a$^2$-a$^3$=a$^4$- defined as in claim 1, and H-G$_2$-OH being defined as G according to claim 1 provided that G is substituted with hydroxy and the carbon atom carrying the hydroxy substituent carries also at least one hydrogen, in the presence of a reducing agent.

11. The process of claim 10, further comprising the step of converting said compound of formula (I) into a therapeutically active non-toxic acid addition salt by treatment with an acid.

12. The process of claim 10, further comprising the step of converting said compound of formula (I) into a therapeutically active non-toxic base addition salt by treatment with alkali.

13. The process of claim 10, further comprising the step of converting the acid addition salt form of compound of formula (I), or stereochemically isomeric forms, thereof, into the free base by treatment with alkali.

14. The process of claim 10, further comprising the step of converting the base addition salt form of compound of formula (I), or stereochemically isomeric forms, thereof, into the free acid by treatment with acid.

15. The process of claim 10, further comprising the step of converting said compound of formula (I), or stereochemically isomeric form thereof, into a different stereochemically isomeric form of said compound of formula (I).

\* \* \* \* \*